US008460651B2

(12) United States Patent  
Marsala et al.

(10) Patent No.: US 8,460,651 B2  
(45) Date of Patent: Jun. 11, 2013

(54) METHODS OF TREATING AMYOTROPHIC LATERAL SCLEROSIS (ALS)

(75) Inventors: Martin Marsala, San Diego, CA (US); Osamu Kakinohana, San Diego, CA (US); Thomas G. Hazel, North Potomac, MD (US); Karl K. Johe, Potomac, MD (US)

(73) Assignees: Neuralstem, Inc., Rockville, MD (US); The Regents of the University of California, Oakland, CA (US)

( * ) Notice: Subject to any disclaimer, the term of this patent is extended or adjusted under 35 U.S.C. 154(b) by 224 days.

(21) Appl. No.: 12/404,841

(22) Filed: Mar. 16, 2009

(65) Prior Publication Data

US 2010/0055075 A1 Mar. 4, 2010

Related U.S. Application Data

(63) Continuation of application No. 11/281,640, filed on Nov. 17, 2005, now Pat. No. 7,691,629.

(60) Provisional application No. 60/629,220, filed on Nov. 17, 2004.

(51) Int. Cl.  
*A01N 63/00* (2006.01)

(52) U.S. Cl.  
USPC ............................ 424/93.7; 435/377; 435/368

(58) Field of Classification Search  
None  
See application file for complete search history.

(56) References Cited

U.S. PATENT DOCUMENTS

| 4,753,635 | A | 6/1988 | Sagen et al. |
|---|---|---|---|
| 4,980,174 | A | 12/1990 | Sagen et al. |
| 5,082,670 | A | 1/1992 | Gage |
| 5,166,065 | A | 11/1992 | Williams et al. |
| 5,175,103 | A | 12/1992 | Lee et al. |
| 5,411,883 | A | 5/1995 | Boss et al. |
| 5,580,777 | A | 12/1996 | Bernard et al. |
| 5,589,376 | A | 12/1996 | Anderson et al. |
| 5,612,211 | A | 3/1997 | Wilson et al. |
| 5,672,499 | A | 9/1997 | Anderson et al. |
| 5,693,482 | A | 12/1997 | Anderson et al. |
| 5,750,376 | A | 5/1998 | Weiss et al. |
| 5,753,505 | A | 5/1998 | Luskin |
| 5,753,506 | A | 5/1998 | Johe |
| 5,770,414 | A | 6/1998 | Gage et al. |
| 5,824,489 | A | 10/1998 | Anderson et al. |
| 5,843,780 | A | 12/1998 | Thomson |
| 5,849,553 | A | 12/1998 | Anderson et al. |
| 5,851,832 | A | 12/1998 | Weiss et al. |
| 5,928,947 | A | 7/1999 | Anderson et al. |
| 5,932,473 | A | 8/1999 | Swiderek et al. |
| 5,958,767 | A | 9/1999 | Snyder et al. |
| 5,981,165 | A | 11/1999 | Weiss et al. |
| 6,040,180 | A | 3/2000 | Johe |
| 6,071,889 | A | 6/2000 | Weiss et al. |
| 6,284,539 | B1 | 9/2001 | Bowen et al. |
| 6,294,346 | B1 | 9/2001 | Weiss et al. |
| 6,399,369 | B1 | 6/2002 | Weiss et al. |
| 6,497,872 | B1 | 12/2002 | Weiss et al. |
| 6,498,018 | B1 * | 12/2002 | Carpenter ............... 435/29 |
| 6,531,464 | B1 | 3/2003 | Szabo et al. |
| 6,699,871 | B2 | 3/2004 | Edmondson et al. |
| 7,101,709 | B2 | 9/2006 | Weiss et al. |
| 7,115,418 | B2 | 10/2006 | Weiss et al. |
| 7,361,505 | B1 | 4/2008 | Weiss et al. |
| 2002/0107273 | A1 | 8/2002 | Nakao et al. |
| 2003/0059369 | A1 | 3/2003 | Kung et al. |

FOREIGN PATENT DOCUMENTS

| EP | 0 233 838 | 8/1987 |
|---|---|---|
| WO | WO 89/03872 | 5/1989 |
| WO | WO 90/06757 | 6/1990 |
| WO | WO 91/02003 | 2/1991 |
| WO | WO 91/09936 | 7/1991 |
| WO | WO 91/17242 | 11/1991 |
| WO | WO 93/01275 | 1/1993 |
| WO | WO 93/09802 | 5/1993 |
| WO | WO 94/02593 | 2/1994 |
| WO | WO 94/03199 | 2/1994 |
| WO | WO 94/04675 | 3/1994 |
| WO | WO 94/10292 | 5/1994 |
| WO | WO 95/13364 | 5/1995 |
| WO | WO 96/09543 | 3/1996 |
| WO | WO 96/15226 | 5/1996 |
| WO | WO 98/48001 | 10/1998 |
| WO | WO 99/01159 | 1/1999 |
| WO | WO 99/11758 | 3/1999 |
| WO | WO 00/17323 | 3/2000 |

OTHER PUBLICATIONS

Chen et al., PLoS ONE (2001) vol. 6, pp. 1-10.*  
Jablonska et al., Acta Neurobiol Exp. (2011) vol. 71, pp. 74-85.*  
Kalladka et al., Neurochem.Int. (2011), doi:10.1016/j.neuint.2011.03.016, 4 pages (available online).*  
Politis, BMC Medicine (2010) 8:80., 5 pages (available online).*  
Ahmed, S. et al., "BDNF Enhances the Differentiation but Not the Survival of CNS Stem Cell-Derived Neuronal Precursors," The Journal of Neuroscience, 15(8): 5765-5778 (1995).

(Continued)

Primary Examiner — Jim Ketter  
(74) Attorney, Agent, or Firm — K&L Gates LLP

(57) ABSTRACT

The invention relates generally to methods of treating spasticity, rigidity, or muscular hyperactivity conditions by introducing a portion of an expanded population of neural stem cells into an area of a recipient spinal cord.

14 Claims, 10 Drawing Sheets

OTHER PUBLICATIONS

Almazan et al., "Epidermal Growth and Bovine Growth Hormone Stimulate Differentiation and Myelination of Brain Cell Aggregates in Culture," Developmental Brain Research, 21:257-264 (1985).

Almazan, G. et al, "Triiodothyronine Stimulation of Oligodendroglial Differentiation and Myelination," Dev. Neurosci, vol. 7, pp. 45-54, 1985.

Anchan, R.M et al, "EFG and TGF-α Stimulate Retinal Neuroepithelial Cell Proliferation in Vitro," Neuron, vol. 6, pp. 923-936, 1991.

Arsenijevic Y. et al, "Isolation of multipotent neural precursors residing in the cortex of the adult human brain," Experimental Neurology, vol. 170, pp. 48-62, 2001.

Avellana-Adalid, V. et al., "Expansion of Rat Oligodendrocyte Progenitors into Proliferative "Oligospheres" that Retain Differentiation Potential," Journal of neuroscience Research, vol. 45, pp. 558-570, 1996, http://www3.interscience.wiley.com/cgi-bin/abstract/67559/ ABSTRACT.

Baas, P.W. et al., "Polarity orientation of microtubules in hippocampal neurons: Uniformity in the axon and nonuniformity in the dendrite," Proc. Natl. Acad. Sci. USA, vol. 85, pp. 8335-8339 (1988).

Baetge, E.E. et al., "Neural Stem Cells for CNS Transplantation," Annals New York Academy of Sciences, vol. 695, pp. 285-291, 1993.

Barlett P. F., "Regulation of Neural Precursor Differentiation in the Embryonic and Adult Forebrain," Clinical and Experimental Pharmacology and Physiology, vol. 22, p. 559-562, 1995.

Barlett, P.F. et al., "Immortalization of mouse neural precursor cells by the c-myc oncogene," Neurobiology, vol. 85, pp. 3255-3259, 1988.

Behl C., "Apoptosis and Alzheimer's disease," Journal of Neural transmission, vol. 107, pp. 1325-1344, 2000.

Bernard, O. et al., "Role of the c-myc and the N-myc Proto-Oncogenes in the Immortalization of Neural Precursors," Journal of Neuroscience Research, vol. 24, pp. 9-20, 1989.

Birren, S.J. et al., "A v-myc-Immortalized Sympathoadrenal Progenitor Cell Line in Which Neuronal Differentiation Is Initiated by FGF but Not NGF," Neuron, vol. 4, pp. 189-201, 1990.

Bredesen, D.E. et al., "Neural Transplantation Using Temperature-sensitive Immortalized Neural Cells: A Preliminary Report," Annals of Neurology, vol. 27, pp. 205-207, 1990.

Bremner, J. D. et al., "Hippocampal volume reduction in major depression," Am. J. Psychiatry, vol. 157, pp. 115-117, 2000.

Brezun, J. et al., "Depletion in serotonin decreases neurogenesis in the dentate gyrus and the subventricular zone of adult rats," Neuroscience, vol. 89, pp. 999-1002, 1999.

Broe, M. et al., "Relationship between DNA fragmentation, morphological changes and neuronal loss in Alzheimer's disease and dementia with Lewy bodies," Acta Neuropathol, vol. 101, pp. 616-624, 2001.

Brustle O., et al., "Neuronal progenitors as tools for cell replacement in the nervous system," Neurobiology 1996, 6:688-695.

Brustle O. et al., "Embryonic Stem Cell-Derived Glial Precursors: A Source of Myelinating Transplants," Science, vol. 285, pp. 754-756, 1999.

Calof A L. et al., "Analysis of neurogenesis in a mammalian neuroepithelium: proliferation and differentiation of an olfactory neuron precursor in vitro," Neuron, vol. 3, pp. 115-127, 1999.

Cambray-Deakin, M.A. The expression of excitatory amino acid binding sites during neuritogenesis in the developing rat cerebellum. Ref. No. 78577. Biol Abstr Vol, 90, 1990.

Cameron H A. et al., "Regulation of neurogenesis by growth factors and neurotransmitters," Journal of Neurobiology, vol. 36, pp. 287-306, 1998.

Cao Q. et al., "Stem Cell Repair of Central Nervous System Injury," Journal of Neuroscience Research, vol. 68, pp. 501-510, 2002.

Carpenter, M. K. et al., "Generation and Transplantation of EGF-Responsive Neural Stem Cells Derived from GFAP-hNGF Transgenic Mice," Experimental Neurology, vol. 148, pp. 187-204, 1997.

Carpenter, M. K. et al., "In Vitro Expansion of a Multipotent Population of Human Neural Progenitor Cells," Experimental Neurology, vol. 158, pp. 265-278, 1999.

Carpenter reexamination U.S. Appl. No. 90/008,862 (reexamination of 6,103,530) entitled "Cultures of Human CNS Neural Stem Cells," filed Oct. 2, 2007.

Castillo, S. O. et al., "Dopamine Biosynthesis Is Selectively Abolished in Substantia Nigra/Ventral Tegmental Area but Not in Hypothalamic Neurons in Mice with Targeted Disruption of the Nurr1 Gene," Molecular and Cellular Neuroscience, vol. 11, pp. 36-46, 1998.

Castillo, S. O. et al., "Organization, Sequence, Chromosomal Localization, and Promoter Identification of the Mouse Orphan Nuclear Receptor Nurr1 Gene," Genomics, vol. 41, pp. 250-257, 1997.

Cattaneo, E. et al., "Proliferation and differentiation of neuronal stem cells regulated by nerve growth factor," Letters to Nature, vol. 347, pp. 762-765, 1990.

Cepko, C.L., "Immortalization of Neural Cells Via Retrovirus-Mediated Oncogene Transduction," Annu. Rev. Neurosci., vol. 12, pp. 47-65, 1989.

Chabot, P. Transient expression of an intermediate filament-associated protein (IFAPa-400) during in vivo and in vitro differentiation of chick embryonic cells derived form neuroectoderm. Ref. No. 78577. Biol Abstr Vol, 90, 1990.

Conover, J.C. et al., "Ciliary neurotrophic factor maintains the pluripotentiality of embryonic stem cells," Development 119, 559-565 (1993).

Coon H G. et al., "Cell cultures of neuroblasts from rat olfactory epithelium that show odorant responses," Neurobiology, vol. 86, pp. 1703-1707, 1989.

Coppell, A. L. et al., "Bi-phasic change in BDNF gene expression following antidepressant drug treatment," Neuropharmcaology, vol. 44, pp. 903-910, 2003.

Cummings, B.J., et al., "Human Neural Stem Cells Differentiate and Promote Locomotor Recovery in Spinal Cord-Injured Mice", Proceedings of the National Academy of Sciences of the United States of America, 102(39):14069-14074, (2005).

Czeh, B. et al., "Stress-induced changes in cerebral metabolites, hippocampal volume, and cell proliferation are prevented by antidepressant treatment with tianepine," PNAS, vol. 98, pp. 12796-12801, 2001.

Davis, A. et al., "A self-renewing multipotential stem cell in embryonic rat cerebral cortex," Letters to Nature, vol. 372, pp. 263-266, 1994.

DiCicco-Bloom, E. et al., "Neuroblast Mitosis in Dissociated Culture: Regulation and Relationship to Differentiation," The Journal of Cell Biology, vol. 110, pp. 2073-2086, 1990.

Drago, J. et al., :Fibroblast Growth Factor-Mediated Prolifereation of Central Nervous System Precursors Depends on Endogenous Production of Insulin-like Growth Factor I, Neurobiology, vol. 88, pp. 2199-2203, 1991.

Drago, J. et al., "A Method for the Isolation of Purified Murine Neuroepithelial Cells From the Developing Mouse Brain," Journal of Neuroscience Methods, vol. 37, pp. 251-256, 1991.

Drago, J. et al., "Basic Fibroblast Growth Factor Upregulates Steady-State Levels of Laminin B1 and B2 Chain mRNA in Cultured Neuroepithelial Cells," Experimental Cell Research, vol. 196, pp. 246-254, 1991.

Drago, J. et al., "Laminin through its Long Arm E8 Fragment Promotes the Proliferation and Differentiation of Murine Neuroepithelial Cells in Vitro," Experimental Cell Research, vol. 192, pp. 256-265, 1991.

D'Sa, C. et al., "Antidepressants and neuroplasticity," Bipolar Disorders, vol. 4, pp. 183-194, 2002.

Dutton, G.R. "Isolation, Culture, and Use of Viable Central nervous System Perikarya," Methods in Neuroscience, vol. 2, pp. 87-102, 1990.

Ehrlich, M.E. et al. "DARPPp-32 development in the caudate nucleus is independent of afferent input from the substantia nigra," Ref. No. 78577. Biol Abstr Vol, 90, 1990.

Eilers M. et al., "Chimaeras of Myc oncoprotein and steroid receptors cause hormone-dependent transformation of cells," Letters to Nature, vol. 340, pp. 66-68, 1989.

Eriksson P S. et al., "Neurogenesis in the adult human hippocampus," Nature Medicine, vol. 4, pp. 1313-1317, 1998.

Escary, J. et al., "Leukaemia inhibitory factor is necessary for maintenance of haematopoietic stem cells and thymocyte stimulation," Nature, vol. 363, pp. 361-364 (1993).

Evans, R.M., "The Steroid and Thyroid Hormone Receptor Superfamily," Articles pp. 889-895 (1988).

Evrard, C. et al., "Immortalization of bipotential and plastic glio-neuronal precursor cells," Proc. Natl. Acad. Sci. USA, vol. 87, pp. 3062-3066 (1990).

Falk A. et al., "Amphiregulin is a mitogen for adult neural stem cells," Journal of Neuroscience Research vol. 69, pp. 757-762, 2002.

Feldman, D.H., et al., "Differentiation of Ionic Currents in CNS Progenitor Cells: Dependence upon Substrate Attachment and Epidermal Growth Factor," Experimental Neurology 140, 206-217 (1996).

Feron F. et al., "Stress induces neurogenesis in non-neuronal cell cultures of adult olfactory epithelium" Neuroscience, vol. 88, pp. 571-583, 1999.

Finger S. et al., "Nimodipine and Neural Grafts," Duke Med Cent Lib 34.P2, p. 208, 1991.

Finley, M. et al., "Synapse Formation and Establishment of Neuronal Polarity by P19 Embryonic Carcinoma and Embryonic Stem Cells," The Journal of Neurosciences, 16(3): 1056-1065 (1996).

Fischer, A.J. et al., "Exogenous Growth Factors Induce the Production of Ganglion Cells at the Retinal Margin," Development, vol. 129, pp. 2283-2291, 2002.

Flax J. D. et al., "Engraftable human neural stem cells respond to developmental cues, replace neurons, and express foreign genes," Nature Biotechnology, vol. 16, pp. 1033-1039, 1998.

Frappaz, D. et al., "Enhancement of Growth of Primary Metastatic Fresh Human Tumors of the Nervous System by Epidermal Growth Factor in Serum-free Short Term Culture," Neurosurgery, vol. 23, pp. 355-359, 1998.

Frederiksen, K. et al., "Immortalization of Precursor Cells for the Mammalian CNS," Neuron, vol. 1, pp. 439-448, 1988.

Fujiwara, Y., et al., "Intravenously Injected Neural Progenitor Cells of Transgenic Rats Can Migrate to the Injured Spinal Cord and Differentiate Into Neurons, Astrocytes and Oligodendrocytes", Neuroscience Letters, 366(3):287-291, (2004).

Gage, F. H. et al., "Isolation, Characterization, and use of Stem Cells From the CNS," Annu. Rev. Neurosci., vol. 18, pp. 159-192, 1995.

Gage, F.H. et al., "Survival and differentiation of adult neuronal progenitor cells transplanted to the adult brain," Proc. Natl. Acad. Sci., vol. 92, pp. 11879-11883, Dec. 1995.

Glasky et al., "Update: Central and Peripheral Nervous Systems AIT-082, a novel purine derivative with neuroregenerative properties," Exp. Opin. Invest. Drugs, vol. 6, pp. 1413-1417, 1997.

Godfraind, C. et al., "In Vivo Analysis of Glial Cell Phenotypes During a Viral Demyelinating Disease in Mice," The Journal of Cell Biology, vol. 109, pp. 2405-2416, 1989.

Goldman S A. et al., "In vitro neurogenesis by neuronal precursor cells derived from the adult songbird brain," The Journal of Neuroscience, vol. 12, pp. 2532-2541, 1992.

Gould E. et al., "Inaugural Article: Adult-generated hippocampal and neocortical neurons in macaques have a transient existence," PNAS, vol. 98, pp. 10910-10917, 2001.

Green S. et al., "Human oestrogen receptor cDNA: sequence, expression and homology to v-erb-A," Nature, vol. 320, pp. 134-139, 1986.

Gritti, A. et al., "Multipotential Stem Cells from the Adult Mouse Brain Proliferate and Self-Renew in Response to Basic Fibroblast Growth Factor," The Journal of Neuroscience, vol. 16, pp. 1091-1100, 1996.

Gu W. et al., "Cortical neurogenesis in adult rats after reversible photothrombotic stroke," Journal of Cerebral Blood Flow and Metabolism, vol. 20, pp. 1166-1173, 2000.

Guentert-Lauber, B. et al., "Responsiveness of Astrocytes in Serum-Free AggregateCultures to Epidermal Growth Factor: Dependence on the Cell Cycle and the Epidermal Growth Factor Concentration," Dev. Neurosci. 7: 286-295 (1985).

Hall et al, 1992, An Introduction to Molecular Neurobiology, p. 357.

Hata, M. et al., "A decrease in the wet-dog shakes response to the second administration of kainic acid in juvenile rats," Ref. No. 31832, Biol Abstr Vol, 92, 1991.

Hauser K F. et al., "Opioids intrinsically inhibit the genesis of mouse cerebellar granule neuron precursors in vitro: differential impact of mu and delta receptor activation on proliferation and neurite elongation," European Journal of Neuroscience, vol. 12, pp. 1291-1293, 2000.

Hermanson, M. et al., "PDGF and its receptors following facial nerve axotomy in rats: expression in neurons and surrounding glia," Exp. Brain Res., vol. 102, pp. 415-422, 1995.

Hollenberg et al., "Epidermal Growth Factor: Receptors in Human Fibroblasts and Modulation of Action by Cholera Toxin," Proc. Nat. Acad. Sci. USA, vol. 70, No. 10, pp. 2964-2968, Oct. 1973.

Honegger, P. et al., "Growth and Differentiation of Aggregating Fetal Brain Cells in a Serum-Free Defined Medium," Nature, vol. 282, pp. 305-308, 1979.

Honkaniemi, J. et al., "Focal brain injury induces multiple immediate early genes encoding zinc finger transcription factors," Molecular Brain Research, vol. 28, pp. 157-163, 1995.

Horcholle-Bossavit, G. et al., "Postnatal development of peroneal motoneurons in the kitten," Ref. No. 78577. Biol Abstr Vol, 90, 1990.

Hoshimaru, M. et al., "Differentiation of the immortalized adult neuronal progenitor ce line HC2S2 into neurons by regulatable suppresision of the v-myc oncogene," Proc. Natl. Acad., vol. 93, pp. 1518-1523, 1996.

Howland et al., "Focal loss of the glutamate transporter EAAT2 in a transgenic rat model of SOD1 mutant-mediated amyotrophic lateral sclerosis (ALS)," PNAS, vol. 99, pp. 1604-1609, 2002.

Hunter, S.F. et al., "Growth factor responses of enriched bipotential glial progenitors," Ref. No. 78577, Biol Abstr Vol, 90, 1990.

Isacson, O., "The production and use of cells as therapeutic agents in neurodegenerative diseases," The Lancet Neurology, 2:417-424, (2003).

Ishibashi et al., "Human Neural Stem/Progenitor Cells, Expanded in Long-Term Neurosphere Culture, Promote Functional Recovery After Focal Ischemia in Mongolian Gerbils," Journal of Neuroscience Research, vol. 78, pp. 215-223, 2004.

Jain, M., et al., "GABAergic Immunoreactivity Is Predominant in Neurons Dervied From Expanded Human Neural Precursor Cells in Vitro", Experimental Neurology, 182(1):113-123,(2003).

Jelitai M. et al., "Regulated appearance of NMDA Receptor Subunits and Channel Functions Duriing in Vitro Neuronal Differentiation," Journal of Neurobiology, vol. 51, pp. 54-65, 2002.

Jin K. et al., "Stem cell factor stimulates neurogenesis in vitro and in vivo." The Journal of Clinical Investigation, vol. 110, pp. 311-319, 2002.

Jin K. et al., "Vascular endothelial growth factor (VEGF) stimulates neurogenesis in vitro and in vivo," PNAS, vol. 99, pp. 11946-11950, 2002.

Johe, K. et al., "Single factors direct the differentiation of stem cells from the fetal and adult central nervous system," Genes & Development, vol. 10, pp. 3129-3140, 1996.

Jones-Villeneuve, et al., "Retinoic Acid Induces Embryonal Carcinoma Cells to Differentiate into Neurons and Glial Cells," The Journal of Cell Biology, vol. 94, pp. 253-262, 1982.

Jung, et al., "Novel pluripotential neural progenitor lines exhibiting rapid controlled differentiation to neurotransmitter receptor-expressing neurons and glia," Eur. J. Neuroscj., vol. 10 pp. 3246-3256 (1998).

Kehl L J. et al., "Neurogenesis in postnatal rat spinal cord: a study in primary culture," Science, vol. 276, pp. 586-589, 1997.

Kempermann, G. et al., "Depressed new neurons-adult hippocampal neurogenesis and a cellular plasticity hypothesis of major depression," Biological Psychiatry, vol. 54, pp. 499-503, 2003.

Kempermann, G. et al., "Genetic determinants of adult hippocampal neurogenesis correlate with acquisition, but not probe trial performance, in the water maze task," European Journal of Neuroscience, vol. 16, pp. 129-136, 2002.

Kershaw, T.R. et al., "Foetal H-2Kb-tsA58 Transgenic Mouse Tissue Develops in a Similar Manner to ISO Geneic Foetal Tissue when Transplanted into Adult Mouse Brain," Duke Med Cent Lib 34.P4, p. 208, 1991.

Kilpatrick et al., "Cloning and Growth of Multipotential Neural Precursors: Requirements for Proliferation and Differentiation," Neuron, vol. 10, pp. 255-265, 1993.

Kilpatrick, T.J., and Bartlett, P.F., "Cloned Multipotential Precursors from the Mouse Cerebrum Require FGF-2, Whereas Glial Restricted Precursors Are Stimulated with Either FGF-2 or EGF," J. Neurosci., 15(5):3653-3661 (1995).

Kilpatrick, T.J., Richards, L.J., and Bartlett, P.F., "The Regulation of Neural Precursor Cells within the Mammalian Brain," Mol. Cell. Neurosci., 6, 2-15, (1995).

Kitani, H. et al., "Isolation and Characterization of Mouse Neural Precursor Cells in Primary Culture," in Vitro Cell. Dev. Biol., vol. 27A, pp. 615-624, 1991.

Kuhn, H. G. et al., "Neurogenesis in the dentate gyrus of the adult rat: age-related decrease of neuronal progeneitor proliferation," The Journal of Neuroscience, vol. 16, pp. 2027-2033, 1996.

Kumar, et al., "Localisation of the oestradiol-binding and putative Dna-binding domains of the human oestrogen receptor," The EMBO Journal, vol. 5, No. 9, pp. 2231-2236, (1986).

Law et al., "Identification of New Brain-Specific Transcription Factor, NURR 1," Molecular Endocrinology, pp. 2129-2135, 1992.

Lee, et al., The v-*myc* oncogene, Oncogene, 18:2997-3003, (1999).

Lee, A. L. et al., "Stress and depression: possible links to neurons death in the hippocampus," Bipolar Disorders, vol. 4, pp. 117-128, 2002.

Lee, J. et al., "Dietary restriction increases the number of newly generated neural cells, and induces BDNF expression, in the dentate gyrus of rats," Journal of Molecular Neuroscience, vol. 15, pp. 99-108, 2001.

Lepore, A.C., et al., "Neural Precursor Cells Can Be Delivered Into the Injured Cervical Spinal Cord by Intrathecal Injection at the Lumbar Cord", Brain Research, 1045(1-2):206-216, (2005).

Lichtenwalner, R. J. et al., "Intracerebroventricular infusion of insulin-like growth factor-1 ameliorates the age-related decline in hippocampal neurogenesis," Neuroscience, vol. 107, pp. 603-613, 2001.

Lindvall, et al., "Stem cell therapy for human neurodegenerative disorders—how to make it work," Nature Med., 10:S42-S50, (2004).

Ling, et al., "Differentiation of Mesencephalic Progenitor Cells into Dopaminergic Neurons by Cytokines," Exp. Neurol., 149, 411-423, (1998).

Littlewood, T.D., et al., "A modified oestrogen receceptor ligan-binding domain as an improved switch for the regulation of heterologous proteins". Nucleic Acids Research. 1995, vol. 23, No. 10, pp. 1686-1690, see abstract.

Llado, J. et al., "Neural Stem Cells Protect Against Glutamate-Induced Excitotoxicity and Promote Survival of Injured Motor Neurons Thrrough the Secretion of Neurotrophic Factors," Molecular and Cellular Neurosciences, 27(3):322-331, (2004).

Lois, et al., "Proliferating subventricular zone cells in the adult mammalian forebrain can differentiate into neurons and glia," Proc. Nat'l Acad. Sci., 90:2074-2077, (1993).

Lovejoy, D.A. et al., "Primary structure of two forms of gonadotropin-releasing hormone from brains of the American alligator," Ref. No. 31832, Biol Abstr Vol, 92, 1991.

Lucassen, P. J. et al., "Hippocampal apoptosis in major depression is a minor event and absent from subareas at risk for glucocorticoid overexposure," American Journal of Pathology, vol. 158, pp. 453-468, 2001.

Lumsden, A. et al., "Patterning the Vertibrate Neuraxis," Science, vol. 274, pp. 1109-1115, Nov. 15, 1996.

Lyman, W.D. et al., "Human Fetal Central Nervous System Organotypic Cultures," Developmental Brain Research, vol. 60, pp. 155-160, 1991.

Ma W. et al., "Acetylcholine stimulates cortical precursor cell proliferation in vitro via muscarinic receptor activation and MAP kinase phosphorylation," European Journal of Neuroscience, vol. 12, pp. 1227-1240, 2000.

Madsen T M. et al., "Increased neurogenesis in a model of electroconvulsive therapy," Biological Psychiatry, vol. 47, pp. 1043-1049, 2000.

Mages, H. et al., "NOT, A Human Immediate-Early Response Gene Closely Related to the Steroid/Thyroid Hormone Receptor NAK1/TR3," Molecular Endocrinology, p. 1583-1591, 1994.

Malberg, J. E. et al., "Chronic antidepressant treatment increases neurogenesis in adult rat hippocampus," The Journal of Neuroscience, vol. 20, pp. 9104-9110, 2000.

Marin N. et al., β-amyloid-induced activation of caspase-3 in primary cultures of rat neurons, Mechanisms of Ageing and Development, vol. 119, pp. 63-67, 2000.

Marsala, M., et al., "Spinal Implantation of hNT Neurons and Neuronal Precursors: Graft Survival and Functional Effects in Rats With Ischemic Spastic Paraplegia", European Journal of Neuroscience, 20(9):2401-2414, (2004).

Masters, B.A. "Insulin-like growth factor I (IFG-I) receptors and IGF-I action in oligodendrocytes from rat brains." Ref. No. 31832, Biol Abstr Vol, 92, 1991.

Mattson, M.P., "Stem cells as therapeutics for neurodegenerative disorders?" Expert Rev. Neurotherapeutics, 267-273, (2001).

Mauerhoff, T. et al., Differential Expression and Regulation of Major Histocompatibility Complex (MHC) Products in Neural and Glial Cells of the Human Fetal Brain, Journal of Neuroimmunology, vol. 18, pp. 271-289, 1988.

Mayo W. et al., "Pregnenolone sulfate and aging of cognitive functions: behavioral, neurochemical, and morphological investigations," Hormones and Behavior, vol. 40, pp. 215-217, 2001.

McCarthy, M. et al., "Infection of Human Neural Cell Aggregate Cultures with a Clinical Isolate of Cytomegalovirus," Journal of Neuropathology and Experimental Neurology, vol. 50, pp. 441-450, 1991.

McKay, R. et al., "Mechanisms Regulating Cell No. And Type in the Mammalian Central Nervous System," Cold Spring Harbor Symposia on Quantitative Biology, vol. LV, pp. 291-301, 1990.

McKay, R., et al., "Stem Cells in the Developing and Adult Brain," (abs.) (1995).

McKay, R., et al., "Stem Cells in the Central Nervous System," Science, 276, pp. 66-71 (1997).

Mervaala, E. et al., "Quantitative MRI of the hippocampus and amygdala in severe depression," Psychological Medicine, vol. 30, pp. 117-125, 2000.

Monnet-Tschudi, F. et al. "Influence of Epidermal Growth Factor on the Maturation of Fetal Rat Brain Cells in Aggregate Culture," Dev Neurosci 1989, vol. 11, pp. 30-40.

Morrison, R.S. et al., "Trophic Stimulation of Cultured Neurons from Neonatal Rat Brain by Epidermal Growth Factor," Science, vol. 238, pp. 72-75, 1987.

Morrison, S.J., et al., "Regulatory Mechanisms in Stem Cell Biology," Cell, vol. 88,287-298, Feb. 7, 1997.

Murphy, M. et al., "Fibroblast Growth Factor Stimulates the Proliferation and Differentiation of Neural Precursor Cells in Vitro," Journal of Neuroscience Research, vol. 25, pp. 463-475, 1990.

Murrell W. et al., "Neurogenesis in adult human," NeuroReport, vol. 7, pp. 1189-1194, 1996.

Mytilineou, C. et al., "Epidermal Growth Factor-Induced Survival and Proliferation of Neuronal Precursor Cells from Embryonic Rat Mesencephalon," Neuroscience Letters, vol. 135, pp. 62-66, 1992.

Nakafuku et al., "Establishment and Characterization of a Multipotential Neural Cell Line That Can Conditionally Generate Neurons, Astrocytes, and Oligodendrocytes in Vitro," Journal of Neuroscience Research, vol. 41, pp. 153-168, 1995.

Nakagawa, S. et al., "Regulation of neurogenesis in adult mouse hippocampus by cAMP and the cAMP reponse element-binding protein," The Journal of Neuroscience, vol. 22, pp. 3673-3682, 2002.

Nestler, E. J. et al., "Neurobiology of Depression," Neuron, vol. 34, pp. 13-25, 2002.

Nibuya M. et al., "Chronic antidepressant administration increases the expression of cAMP response element binding protein (CREB) in rat hippocampus." The Journal of Neuroscience, vol. 16, pp. 2365-2372, 1996.

Nielsen, F.C. et al., "Receptor Binding, Endocytosis, and Mitogenesis of Insulin-Like Growth Factors I and II in Fetal Rat Brain Neurons," Journal of Neurochemistry, vol. 56, pp. 12-21, 1991.

Ohkura, et al., "Structure, mapping and expression of a human NOR-1 gene, the third member of the Nur77/NGFI-B family," Biochim. Biophys. Acta, 1308:205-214, (1996).

Oka, S., et al, "Autologous Transplantation of Expanded Neural Precursor Cells Into the Demyelinated Monkey Spinal Cord", Brain Research, 1030(1):94-102, (2004).

Okabe, et al., "cDNA Cloning of a NGFI-B/nur77-Related Transcription Factor from an Apoptotic Human T Cell Line," J. Immunol., 154:3871-3879, (1995).

Okano et al., "Neural stem cells and regeneration of injured spinal cord," Kidney International, vol. 68, pp. 1927-1931, 2005.

Okano, H., "Neural stem cells: progression of basic research and perspective for clinical application," Keio Journal of Medicine, vol. 51, pp. 115-128, 2002.

Palmer T D. et al., "The Adult Rat Hippocampus Contains Primordial Neural Stem Cells," Molecular and Cellular Neuroscience 8, 389-404 (1997).

Palmer T D. et al., "Fibroblast growth factor-2 activates a latent neurogenic program in neural stem cells from diverse regions of the adult CNS," the Journal of Neuroscience, vol. 19, pp. 8487-8497, 1999.

Park K. et al., "Global gene and cell replacement strategies via stem cells," Gene Therapy, vol. 9, pp. 613-624, 2002.

Pena de Ortiz et al., "HZF-3, an immediate-early orphan receptor homologous to NURR1/NOT: Induction upon membrane depolarization and seizures," Mol. Brain Res. 38:1-13 (1996).

Perrone-Capano et al., "Epigenetic factors and midbrain dopaminergic neurone development," Bioessays vol. 18 No. 10 pp. 817-824 (1996).

Peterson D. A. et al., "Trophic factor therapy for neuronal death," Alzheimer Disease, $2^{nd}$ Edition, Chapter 25, pp. 373-388, 1999.

Pham, K. et al., "Repeated restraint stress suppresses neurogenesis and induces biphasic PSA-NCAM expression in the adult dentate gyrus," European Journal of Neuroscience, vol. 17, pp. 879-886, 2003.

Piescinski, P. et al., "Neurogenesis of the amygdaloid complex in the rhesus monkey," Society for Neuroscience Abstracts, vol. 16, p. 1147, 1990.

Pollerberg et al., "Generation of Cell Lines From Embryonic Quail Retina Capable of Mature Neuronal Differentiation," Journal of Neuroscience Research, vol. 41, pp. 427-442, 1995.

Pucilowski, O. et al., Decreased hyperthermic effect of MK801 in selectively bred hypercholinergic rats, Ref. No. 31832, Biol Abstr Vol, 92, 1991.

Puliam, L. et al., "A Normal Human Brain Cell Aggregate Model for Neurobiological Studies," Journal of Neuroscience Research, vol. 21, pp. 521-230, 1988.

Qian, X et al., "FGF2 Concentration Regulates the Generation of Neurons and Glia from Multipotent Cortical Stem Cells," Neuron, vol. 18, pp. 81-93, Jan. 1997.

Qu, T. et al., "Human neural stem cells improve cognitive function of aged brain," NeuroReport, vol. 12, pp. 1127-1132, 2001.

Raina, A K. et al., "Abortive apoptosis in Alzheimer's disease," Acta Neuropathol, vol. 101, pp. 305-310, 2001.

Rajan et al., "Neural Stem Cells and Their Munipulation," (2006) Methods in Ezymol. 419:23-52.

Rakic, P. "Radial Versus Tangential Migration of Neuronal Clones in the Developing Cerebral Cortex," Proc. Natl. Acad. Sci, USA, vol. 92, pp. 11323-11327, Dec. 1995.

Rao et el., "Immortalization and Controlled in Vitro Differentiation of Murine Multipotent Neural Crest Stem Cells," (1997) J. Neurobiol. 32, 722.

Rathbone M P. et al., "Trophic effects of purines in neurons and glial cells," Progress in Neurobiology, vol. 59, pp. 663-690, 1999.

Ray, J. and Gage, F.H., "Spinal Cord Neuroblasts Proliferate in Response to Basic Fibroblast Growth Factor," J. Neurosci. 14(6): 3548-3564 (1994).

Ray, J. Peterson, D., Schinstine, M. & Gage, F., "Proliferation, differentiation, and long-term culture of primary hippocampal neurons," Proc. Natl. Acad. Sci. USA vol. 90, pp. 3602-3606 (1993).

Reichmann et al., "Activation of an Inducible c-FosER Fusion Protein Causes Loss of Epithelial Polarity and Triggers Epithelial-Fibroblastoid Cell Conversion," (1992) Cell vol. 71, pp. 1103-1116.

Renoncourt et al., Neurons derived in vitro from ES cells express homeoproteins characteristic of motoneurons and interneurons (1998) Mechanisms of Development 79 pp. 185-197.

Resnick, J et al., "Long-term proliferation of mouse primordial germ cells in culture," Nature, vol. 359, pp. 550-551, Oct. 8, 1992.

Rettig, W.J. et al., "Cell Type-specific Control of Human Neuronectin Secretion by Polypeptide mediators and Phorbol Ester," The Journal of Histochemistry and Cytochemistry, vol. 37, pp. 1777-1786, 1989.

Rettig, W.J. et al., "Stimulation of Human Neuronectin Secretion by Brain-Derived Growth Factors," Brain Research, vol. 487, pp. 171-177, 1989.

Reynolds, B.A. et al., "A Multipotent EFG-Responsive Striatal Embryonic Progenitor Cell Produces Neuron and Astrocytes," The Journal of Neuroscience, vol. 12, pp. 4565-4574, 1992.

Reynolds, B.A. et al., "A Non-Transformed, Growth Factor Dependent Stem Cell Line Derived From the Embryonic Mouse CNS Produces Neurons, Astrocytes and Oligodendrocytes," Duke Med Cent Lib 34.P3, p. 208, 1991.

Reynolds, B.A. et al., "EGF- and TFGα-responsive striatal embryonic progenitor cells produce both neurons and astocytes," Society for Neuroscience Abstracts, vol. 16, p. 1147, 1990.

Reynolds, B.A. et al., "Generation of Neurons and Astocytes from Isolated Cells of the Adult Mammalian Central Nervous System," Science, vol. 255, pp. 1707-1709, 1992.

Reynolds, B.A. et al., "Clonal and Population Analyses Demonstrate That an EGF-Responsive Mammalian Embryonic CNS Precursor Is a Stem Cell," Developmental Biology 175, 1-13 (1996).

Righi et al., myc-Immortalized Microglial Cells Express a Functional Platelet-Activating Factor Receptor (1995) J. Neurochem. 64, 121-129.

Rind H. et al., "Synaptic Targeting of Retrogradely Transported Trophic Factors in Mononeurons: Comparison of Glial Cell Line-Derived Neurotrophic Factor, Brain-Derived Neurotrophic Factor, and Cardiotrophin-1 with Tetanus Toxin," the Journal of Neuroscience, vol. 25, pp. 539-549, 2005.

Romand, R. et al., "Development of tonotopy oin the inferior colliculus: 1. Electrophysiological mapping in house mice," Ref. No. 78577. Biol Abstr Vol, 90, 1990.

Roth, K. A., "Caspases, apoptosis, and Alzheimer disease: causation, correlation, and confusion," Journal of Neuropathology and Experimental Neurology, vol. 60, pp. 829-838, 2001.

Rothstein J.D. et al., "Decreased Glutamate Transport by the Brain and Spinal Cord in Amyotrophic Lateral Sclerosis," The New England Journal of Medicine, vol. 326, pp. 1464-1468, 1992.

Roy N S, et al., "In vitro neurogenesis by progenitor cells isolated from the adult human hippocampus," Nature Medicine, vol. 6, pp. 271-277, 2000.

Rozental R. et al., "Differentiation of hippocampal progenitor cells in vitro: temporal expression of intercellular coupling and voltage- and ligand-gated responses," Developmental Biology, vol. 167, pp. 350-362, 1995.

Rudland, P.S. et al., "Growth Control in cultured Mouse Fibroblasts: Induction of the Pleiotypic and Mitogenic Responses by a Purified Growth Factor," Proc. Nat. Acad. Sci., vol. 71, No. 7, pp. 2600-2604, Jul. 1974.

Rutka, J.T. et al., "Characterization of Fetal Human Brain Cultures," Dev. Neurosci., vol. 9, pp. 1541-1573, 1987.

Ryder et al., "Establishment and Characterization of Multipotent Neural Cell Lines Using Retrovirus Vector-Mediated Oncogene Transfer," (1990) J. Neurobiol vol. 21, No. 2, pp. 356-375.

Sabate, O., Horellou, P., Vigne, E., Colin, P., Perricaudet, M., Buc-Caron, M.-H. & Mallet, J., "Transplantation to the rat brain of human neural progenitors that were genetically modified using adenoviruses," Nature Genetics 9, 256-260 (1995).

Sah et al., "Bipotent progenitor cell lines from the human CNS," (1997) Nature Biotech. 15:574.

Sales, N. et al., "Neutral endopeptidase 24.11 in rat peripheral tissues: comparative localization bby "ex vivo" and "In vitroautoradiography, Ref. No. 31832, Biol Abstr Vol, 92, 1991.

Saneto, R.P. et al., "Insulin/Insulin-Like Growth Factor I and Other Epigenetic Modulators of Myelin Basic Protein Expression in Isolated Oligodendrocyte Progenitor Cells," Journal of Neuroscience Research, Vo. 21, pp. 210-219, 1988.

Santarelli, L. et al., "Requirement of hippocampal neurogenesis for the behavioral effects of antidepressants," Science, vol. 301, pp. 805-809, 2003.

Sato, H. et al., "Somatostatin receptors in the senescent rat brain: A quantitative autoradiographic study," Ref. No. 31832, Biol Abstr Vol, 92, 1991.

Satoh M. et al., "Promotion of neurogenesis in mouse olfactory neuronal progenitor cells by leukemia inhibitory factor in vitro," Neuroscience Letters, vol. 225, pp. 165-168, 1997.

Saucedo-Cardenas et al., "Cloning and structural organization of the gene encoding the murine nuclear receptor transcription factor, NURR1," Gene 187:135-139 (1997).

Saucedo-Cardenas et al., "Nurr 1 is essential for the induction of the dopaminergic phenotype and the survival of ventral mesencephalic late dopaminergic precursor neurons," Proc. Natl. Acad. Sci. USA 95:4013-4018 (1998).

Scearce et al., "RNR-1, a Nuclear Receptor in the NGFI-B/Nur77 Family That Is Rapidly Induced in Regenerating Liver," J. Biol. Chem. vol. 268, No. 12, pp. 8855-8861 (1993).

Schapira, A., "Pathogenesis of Parkinson's disease," Bailliere's Clin. Neurol. vol. 6, No. 1, pp. 15-36 (1997).

Schinstine, M. et al., "Expression of Neuronal Antigens by Astrocytes Derived from EGF-Generated Neuroprogenitor Cells," Experimental Neurology 141, 67-78 (1996).

Schlaggar, B.L. et al., "Potential of Visual Cortex to Develop an Array of Functional Units Unique to Somatosensory Cortex," Science, vol. 252, pp. 1556-1560 (1991).

Scott B W. et al., "Neurogenesis in the dentate gyrus of the rat following electroconvulsive shock seizures," Experimental Neurology, vol. 165, pp. 231-236, 2000.

Seaberg R M. et al., "Adult rodent neurogenic regions: the ventricular subependyma contains neural stem cells, but the dentate gyrus contains restricted progenitors," The Journal of Neuroscience, vol. 22, pp. 1784-1793, 2002.

Seigel, G.M. et al., "Differentiation of oncogenically altered chick neuroretinal cells by succinylated concanavalin A," Society for Neuroscience Abstracts, vol. 16, p. 1147, 1990.

Selvakumarun et al., "Myeloblastic Leukemia Cells Conditionally Blocked by Myc-Estrogen Receptor Chimeric transgenes for Terminal Differentiation Coupled to Growth Arrest and Apoptosis," (1993) Blood vol. 81, No. 9, pp. 2257-2262.

Shingo T. et al., "Erythropoietin regulates the in vitro and in vivo production of neuronal progenitors by mammalian forebrain neural stem cells," The Journal fo Neuroscience, vol. 21, pp. 9733-9743, 2001.

Shirayama, Y. et al., "Brain-derived neurotrophic factor produces antidepressant effects in behavioral models of depression," The Journal of Neuroscience, vol. 22, pp. 3251-3261, 2002.

Shors T J. et al., "Neurogenesis in the adult is involved in the formation of trace memories," Nature, vol. 410, pp. 372-376, 2001.

Shou J. et al., "BMPs inhibit neurogenesis by a mechanism involving degradation of a transcription factor," Nature Neuroscience, vol. 2, pp. 339-345, 1999.

Sigma-Aldrich, Material Safety Data Sheet for Ethylenediaminetetraacetic Acid, for Complexometry, pp. 1-7 (1995).

Silani, V. et al., "Human Neuronal Cells in Culture: From Concepts to Basic Methodology," Boll. 1st. Sieroter. Mila., vol. 69, pp. 309-313, 1990.

Snyder et al., "Taking Stock and Planning for the Next Decade: Realistic Prospects for Stem Cell Therapies for the Nervous System," (2004) J. Neurosci. Res. 76:157-168.

Sorensen, K.A. et al., "Postembryonic neurogenesis in the Brain of Manduca Sexta," Society for Neuroscience Abstracts, vol. 16, p. 1147, 1990.

Sternfeld, M.D. et al., "Cultured Human Retinal Pigment Epithelial Cells Express Basic Fibroblast Growth Factor and its Receptor," Current Eye Research, vol. 8, pp. 1029-1037, 1989.

Stewart, J.S. et al., "Olfactory bulb and sensory epithelium in goldfish: Morphological alterations accompanying growth," Ref. No. 78577. Biol Abstr Vol, 90, 1990.

Stone et al., "Definition of Regions in Human c-mycThat Are Involved in Transformation and Nuclear Localization," Molecular and Cellular Biology vol. 7, No. 5, pp. 1697-1709, 1987.

Svendsen, C.N. & Rosser, A.E., "Neurones from stem cells?" Trends in Neuroscience vol. 18, No. 11, pp. 465-466 (1995).

Svendsen, C.N., Fawcett, J.W., Bentlage, C. & Dunnett, S.B., "Increased survival of rat EGF-generated CNS precursor cells using B27 supplemented medium," Exp. Brain Res. 102: 407-414 (1995).

Svendsen, C.N. et al., "Survival and Differentiation of Rat and Human Epidermal Growth Factor-Responsive Precursor Cells Following Grafting into the Lesioned Adult Central Nervous System," Experimental Neurology 137, 376-388 (1996).

Svendsen, C.N. et al., "A new method for the rapid and long term growth of human neural prescursor cells," Journal of Neuroscience Methods 85 (1998) 141-152.

Takahashi J. et al., "Retinoic acid and neurotrophies collaborate to regulate neurogenesis in adult-derived neural stem cell cultures," J Neurobiol, vol. 38, pp. 65-81, 1999.

Takahashi, T. et al., "Cell cycle kinetics of the E14 murine cerebral ventricular zone: estimates based upon S-Phase labeling with BUdR," Society for Neuroscience Abstracts, vol. 16, p. 1147, 1990.

Takeichi and Okada, "Roles of magnesium and calcium ions in cell-to-substrate adhesion," Experimental Cell Research 74, pp. 51-60, 1972.

Taupin P, et al., "FGF-2-responsive neural stem cell proliferation requires CCg, a novel autocrine/paracrine cofactor," Neuron, vol. 28, pp. 385-397, 2000.

Taylor, M. et al., "Induction of Differentiation of Rat Retinal, Germinal, Neuroepithelial Cells by dbcAMP," Journal of Neurobiology, vol. 21, pp. 470-481, 1990.

Temple, S., "Division and Differentiation of Isolated CNS Blast Cells in Microculture," Nature, vol. 340, pp. 471-473-1989.

Temple, S. et al., "Vertebrate neural progenitor cells: subtypes and regulation," Current Opinion in Neurobiology 1996, 6:11-17.

Tenot, M. et al., Epidermal Growth Factor Enhances the Expression of an Edogenous Lectin in Aggregating Fetal Brain Cell Cultures, Journal of Neurochemistry, vol. 53, pp. 1435-1441, 1989.

Torelli, S. et al., "Human Fetal Brain Cultures: A Model to Study Neural Proliferation, Differentiation and Immunocompetence," Adv. Exp. Med. Biol, vol. 296, pp. 121-134, 1991.

Torres, R.A. et al., "Alteration of Neuronal Regulation of Astrocytoma Proliferation by Insertional Mutagenesis," Society for Neuroscience Abstracts, vol. 16, p. 1147, 1990.

Turner M.R. et al., "Abnormal cortical excitability in sporadic but not homozygous D90A SOD1 ALS," J Neurol Neurosurg Psychiatry, vol. 76, pp. 1279-1285, 2005.

Unsicker et al., "Growth factor function in the development and maintenance of midbrain dopaminergic neruons: concepts, facts and prospects for TGF-β," Ciba Found. Symp. 196, pp. 70-84 (1996).

Van Praag et al., "Running enhances neurogenesis, learning, and long -term potentiation in mice," PNAS, vol. 96, pp. 13427-13431, 1999.

Van Praag et al., "Running increases cell proliferation and neurogenesis in the adult mouse dentate gyrus," Nature Neuroscience, vol. 2, pp. 266-270, 1999.

Vescovi et al., "Isolation and Cloning of Multipotential Stem Cells from the Embryonic Human CNS and Establishment of Transplantable Human Neural Stem Cell Lines by Epigenetic Stimulation," (1999) Exp. Neurol. 156, 71-83.

Vescovi, A.L., Reynolds, B.A., Fraser, D.D., and Weiss, S., "bFGF Regulates the Proliferative Fate of Unipotent (Neuronal) and Bipotent (Neuronal/Astroglial) EGF-Generated CNS Progenitor Cells," Neuron vol. 11, pp. 951-966 (1993).

Vicario-Abejon, C., Johe, K., Hazel, T., Collazo, D. & McKay, R., "Functions of Basic Fibroblast Growth Factor and Neurotrophins in the Differentiation of Hippocampal Neurons," Neuron vol. 15, 105-114 (1995).

Villa, A. et al., "Intracellular calcium ion stores in chicken purkinje neurons; Differential distribution of the low affinity-high capacity calcium binding protein, calsequestrin, of calcium ATPase and of the ER luminal protein," Bip. Ref. No. 31832, Biol Abstr Vol, 92, 1991.

Von Frijtag, J. C. et al., "Chronic imipramine treatment partially reverses the lnog-term changes of hipocampal synaptic plasticity in socially stressed rats," Neuroscience Letters, vol. 309, pp. 153-156, 2001.

Von Visger, J.R. et al., "Differentiation and Maturation of Astrocytes Derived from Neuroepithelial Progenitor Cells in Culture," Experimental Neurology 128: 34-40, 1994.

Vu, E.T. et al., "Evidence for a Computational Distinction Between Proximal and Distal Neuronal Inhibition," Science, vol. 255, pp. 1710-1712, 1992.

Wagner et al, "Induction of a midbrain dopaminergic phenotype in Nurr1-overexpressing neural stem cells by type 1 astrocytes,"1999, Nat. Biotech., vol. 17:, pp. 653-659.

Wainer, B.H. et al., "In vitro cell cultures as model of the basal forebrain," Adv Exp Med Biol., vol. 295, pp. 415-437, 1991.

Wang et al., "A regulatory system for use in gene transfer," (1994) PNAS vol. 91, pp. 8180-8184.

Wang et al., "Induction of dopaminergic neurono phenotype in the midbrain by Sonic hedgehog protein," Nature Medicine, vol. 1, pp. 1184-1188, 1995.

Watanabe, R.T. et al., "Rod Photoreceptor development in vitro: intrinsic properties of proliferating neuroepithelial cells change as development proceeds in the rat retina," NeuralCulture, Abstract, 1990.

Watt et al., "Nucleotide sequence of cloned cDNA of human c-myc oncogene," Nature 303: 725-728, 1983.

Weiss et al., "Multipotent CNS Stem Cells Are Present in the Adult Mammalian Spinal Cord and Ventricular Neuroaxis," The Journal of Neuroscience, vol. 16, pp. 7599-7609, 1996.

Weiss et al. reexamination U.S. Appl. No. 90/008,580 (reexamination of 5,851,832) entitled "In Vitro Growth and Proliferation of Multipotent Neural Stem Cells and Their Progeny," filed Apr. 5, 2007.

Weiss et al. reexamination U.S. Appl. No. 90/008,367 (reexamination of 6,294,346) entitled "Use of Multipotent Neural Stem Cells and Their Progeny for the Screening of Drugs and Other Biological Agents," filed Dec. 7, 2006.

Weiss et al. reexamination U.S. Appl. No. 90/008,581 (reexamination of 6,497,872) entitled "Neural Transplantation Using Proliferated Multipotent Neural Stem Cells and Their Prodigy," filed Apr. 5, 2007.

Weiss et al. reexamination U.S. Appl. No. 90/008,366 (reexamination of 7,101,709) entitled "Methods of Screening Biological Agents," filed Dec. 7, 2006.

Weiss, S. et al., "Is there a neural stem cell in the mammalian forebrain?" TINS vol. 19, No. 9, 1996, pp. 387-393.

Weissman, I.L., "Translating Stem and Progenitor Cell Biology to the Clinic: Barriers and Opportunities," Science (2000) 287:1442-1446.

Wohl C A, et al., "Retinoic acid enhances neuronal proliferation and astroglial differentiation in cultures of Cns stem cell-derived precursors," J Neurobiol, vol. 37, pp. 281-290, 1998.

Wolswijk et al., "Identification of an adult-specific glial progenitor cell" Development, 105:387-400 (1989).

Xing et al., "Rat nurr1 is prominently expressed in perirhinal cortex, and differentially induced in the hippocampal dentate gyrus by electroconvulsive vs. kindled seizures," Molecular Brain Research, vol. 47, pp. 251-261, 1997.

Xu et al., "The extremem C terminus of progesterone receptor contains a transcriptional repressor domain that functions through a putative corepressor," Proc. Natl. Acad. Sci., vol. 93, pp. 12195-12199, 1996.

Xu, L. et al., "Glucocorticoid receptor and protein/RNA synthesis-dependent mechanisms underlie the control of synaptic plasticity by stress," PNAS, vol. 95, pp. 3204-3208, 1998.

Yamada et al., "NMDA receptor mediated Ca2+ responses in neurons differentiated from p53-/-immortalized Murin neural stem cells," (1999) Neurosci. Letters 264, pp. 165-167.

Yan J. et al., "Differentiation and Tropic/Trophic Effects of Exogenous Neural Precursors in the Adult Spinal Cord," vol. 480, pp. 101-114, 2004.

Yan, J. et al., "Grafted Human Neural Stem (NS) Cells Differentiate Into Neurons, Migrate Long Distance and Project Axons in Spinal Cord and the Roots of Adult Rats," Program No. 150.19, Abstract Viewer/Ininerary Planner. Society for Neuroscience, 2003.

Ye et al., "FGF and Shh Signals Control Dopaminergic and Serotonergic Cell Fate in the Anterior Neural Plate," Cell vol. 93:755-766 (1998).

Yoshimoto, Y. et al, "The Effect of Cool Storage on the Survivability of Intraventricular Rat Fetal Ventral Mesencephalic Graft," Duke Med Cent Lib 34.P1, p. 208, 1991.

Zetterström et al., "Cellular expression of the immediate early transcription faxtors Nurr 1 and NGFI-B suggests a gene regulatory role in several brain regions including the nigrostriatal dopamine system," Molecular Brain Research, vol. 41, pp. 111-120, 1996.

Zetterström et al., "Dopamine Neuron Agenesis in Nurr1-Deficient Mice," Science 276:248-250 (1997).

Zhang, R. et al, "A nitric oxide donor induces neurogenesis and reduces functional deficits after stroke in rats," Ann. Neurol., vol. 50, pp. 602-611, 2001.

Bjerkvig et al., "Reaggregation of Fetal Rat Brain Cells in a Stationary Culture System I: Methodology and Cell Identification," In Vitro Cellular & Development Biology, 22:4 180-192 (1986).

Dahlstrand et al., "Nestin mRNA expression correlates with the central nervous system progenitor cell state in many, but not all, regions of developing central nervous system," Developmental Brain Research 84:109-129 (1995).

Doering et al., "Isolation and identification of neuroblast precursor cells from mouse neopallium," Developmental Brain Research 5:229-233 (1982).

Eccleston et al., "Requirements for Brain Cell Attachment, Survival and Growth in Serum-Free Medium: Effects of Extracellular Matrix, Epidermal Growth Factor and Fibroblast Growth Factor" Dev. Neurosci 7:308-322 (1985).

Engebraaten et al., "Effects of EGF, bFGF, NGF and PDGF(bb) on cell proliferative, migratory and invasive capacities of human brain-tumor biopsies in vitro," Int. J. Cancer, 53:209-214 (1993).

Hockfield et al., "Identification of Major Cell Classes in the Developing Mammalian Nervous System," The Journal of Neuroscience 5:12 3310-3328 (1985).

Law, et al., "Molecular Cloning of a Novel Member of theNuclear Receptor Superfamily Realted to the Orphan Receptor, TR2," Gene Expr., vol. 4, pp. 77-84, (1994).

Lendahl et al., "CNS Stem Cells Express a New Class of Intermediate Filament Protein," Cell 60:585-595 (1990).

Math et al., "The Role of Cell-cell Contact in "Contact" Inhibition of Cell Division: A Review and New Evidence," J. Cell. Physiol., 79:189-210, (1971).

McConnell, S., "Constructing the Cerebral Cortex: Neurogenesis and Fate Determination," Neuron, vol. 15, 761-768, Oct., 1995.

Morshead et al., "Postmitotic Death is the Fate of Constitutively Proliferating Cells in the Subependymal Layer of the Adult Mouse Brain," The Journal of Neuroscience 12(1):249-256 (1992).

Morshead et al., "Neural Stem Cells in the Adult Mammalian Forebrain: A Relatively Quiescent Subpopulation of Subependymal Cells," Neuron 13:1071-1082 (1994).

Nolte, J., "Introduction to the Nervous System," The Human Brain an Introduction to Its Functional Anatomy, Fourth Edition pp. 1-35 (1999).

Price, "Brain Stems," Current Biology 5:3 232-234 (1995).

Redies et al., "Differentiation and Heterogeneity in T-Antigen Immortalized Precursor Cell Lines From Mouse Cerebellum," Journal of Neuroscience Research 30:601-615 (1991).

Stemple, D. et al., "Neural Stem Cells Are Blasting Off," Neuron, vol. 18, 1-4, Jan. 1997.

Tohyama et al., "Nestin Expression in Embryonic Human Neuroepithelium and in Human Neuroepithelial Tumor Cells," Laboratory Investigation 66:3 303-313 (1992).

Trenkner et al., "Cell Reaggregation and Migration, Fiber and Synapse Formation," The Journal of Cell Biology 75:915-940 (1977).

Tropepe, V. et al., "Direct Neural Fate Specification from Embryonic Stem Cells: A Primitive Mammalian Neural Stem Cell Stage Acquired through a Default Mechanism," Neuron, vol. 30, 65-78, Apr. 2001.

Zeller et al., "The Timely Expression of Myelin Basic Protein Gene in Cultured Rat Brain Oligodendrocytes is Independent of Continuous Neuronal Influences," The Journal of Neuroscience 5:11 2955-2962 (1985).

G. Rappa, et al., "Efficient Expansion and Gene Transduction of Mouse Neural Stem/Progenitor cells on Recombinant Fibronectin," Neuroscience 124 (2004) 823-830.

P. F. Bartlett, et al., "Immortalization of Mouse Neural Precursor Cells by the c-myc Oncogene," Pro. Natl. Acad. Sci. USA, vol. 85, pp. 3255-3259, May 1998 Neurobiology.

* cited by examiner

FIG. 3A
FIG. 3B
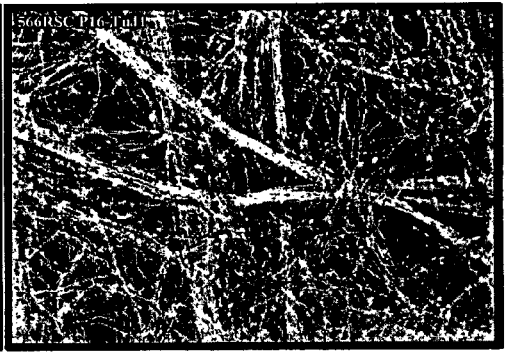
FIG. 3C
FIG. 3D

METHODS OF TREATING AMYOTROPHIC LATERAL SCLEROSIS (ALS)

CROSS REFERENCE TO RELATED APPLICATIONS

The present application claims priority to co-pending U.S. patent application Ser. No. 11/281,640, filed Nov. 17, 2005, which claims priority to U.S. Provisional Patent Application Ser. No. 60/629,220, filed Nov. 17, 2004, each of which are incorporated herein by reference in their entireties.

This work was supported by grants from the United States Government funded through the National Institutes of Health. The U.S. Government has certain rights in this invention.

BACKGROUND

The disclosed methods relate to methods of treating disorders through transplantation of cells that are uniquely beneficial for such treatment methods. In particular, the disclosed methods provide methods of treating neurodegenerative conditions with neural stem cells (NSCs).

Neurodegenerative disorders are characterized by conditions involving the deterioration of neurons as a result of disease, hereditary conditions or injury, such as traumatic or ischemic spinal cord or brain injury.

The circuitry of the spinal cord that governs contraction of skeletal muscles of the limbs, involves excitatory motor neurons and inhibitory GABAergic (i.e., GABA-producing) and glycinergic (i.e., glycine-producing) inter-neurons. A motor neuron is a nerve that originates from the anterior horn of the gray matter of the spinal cord. The axon of the motor neuron emerges from a segment of the spinal cord as an efferent motor fiber that innervates muscle fibers. Impulses conducted by the motor neuron stimulate the muscle fibers to contract. GABA, gamma-amino butyric acid, is a naturally occurring metabolite of the mammalian nervous system which acts as a neurotransmitter to inhibit or dampen the nerve conduction of electrical potential. Loss of GABAergic interneurons results in dysregulation of the inhibitory tonality of the motor neuron-evoked muscle contractions. Without the control exerted by inhibitory interneurons on excitatory neurons, an over-firing of excitatory neurons occurs leading to spastic uncontrolled contraction or uncontrolled rigidity of the muscles of the limbs. Loss of motor neurons results in flaccid paraplegia in which the subjects cannot contract the muscles and are thereby unable to move.

One instance in which GABAergic interneurons are damaged in the spinal cord includes a complication associated with a transient cross-clamping of the descending thoracic or thoracoabdominal aorta. Such cross-clamping is a necessary step in vascular surgery to repair aneurysms of thoracic or thoracoabdominal aorta. For the duration of the cross-clamping, a portion of the spinal cord does not receive blood circulation and can become ischemic. Depending on the duration of the ischemic interval, subsequent neurodegenerative dysfunction may be expressed neurodegeneratively as paraparesis or fully-developed spastic or flaccid paraplegia.

While the mechanism leading to ischemia-induced neuronal degeneration is only partially understood and may involve excessive release/activity of excitatory amino acids, prostaglandins and/or oxygen free radicals, the neuronal population of spinal cord affected by transient ischemic insult are well defined. For example, histopathological analysis of spinal cord taken from animals with fully developed spastic paraplegia shows a selective loss of small inhibitory neurons; however, alpha-motoneurons persist in previously ischemic spinal segments. Similar spinal neuronal pathology in human subjects having spinal ischemic injury has been described.

In contrast, in animals with flaccid paraplegia, pan-necrotic neurodegenerative changes are seen affecting both small inhibitory and excitatory interneurons as well as ventral motor neurons. During the period of neuronal degeneration after spinal ischemia, an injury-dependent activation of local microglia and inflammatory changes, such as infiltration with macrophages, is also seen as in focal or global brain ischemia. Depending on the extent of injury, the inflammatory changes typically peak between two to seven days after ischemic insult and then show gradual loss of inflammatory elements over two to four weeks of post-ischemic period.

In the past two to three decades, a considerable effort has been made to assess in animal models the therapeutic potential of spinal grafting of a variety of materials. Thus, cell lines or acutely isolated spinal cord fetal tissue have been delivered to injured regions and direct spinal gene therapy has also been used to ameliorate neurodegenerative dysfunctions in several models of spinal injury, including mechanical traumatic injury, chemically lesioned spinal cord or genetically manipulated animals with progressive α-motoneuronal degeneration (ALS transgenic mice or rat).

In general, studies demonstrate long-term survival and preservation of neuronal phenotypes in grafts generated from fetal tissue, but not from neural precursors that have been expanded in vitro. In fact, only limited neuronal differentiation and maturation of neural precursors expanded in vitro and grafted into mechanically or chemically injured spinal cord has been demonstrated. Cells preferentially differentiate into non-neuronal cell types. While the mechanism of this preferential non-neuronal differentiation is not completely understood, it is hypothesized that a local release of pro-inflammatory cytokines (such as TNFα, TGFβ) at the site of previous injury is likely involved.

Neurodegeneration represents a particularly challenging biological environment for cell therapy and cell death signals present in established neurodegenerative disease (Rothstein et al., 1992; Howland et al., 2002; Turner et al., 2005) may be incompatible with graft survival. In addition, the adult spinal cord is viewed as lacking cells and/or signals allowing regeneration (Park et al., 2002), and the majority of NSC grafting studies have shown poor or restricted differentiation (Cao et al., 2002; Yan et al., 2003; Yan et al., 2004).

One of the major problems in cell therapeutics is low cell survival (less than 5%) of the cells grafted. All of the grafted cells to date undergo significant cell death shortly after injection in vivo. Thus, in order to deliver an effective dose of cells, the final dose must be injected at least 20 times. This, in turn, requires a much larger scale of cell manufacturing which poses further regulatory and economic obstacles. Furthermore, the survival rate of such cells in vivo has not been able to be maintained. Failure to demonstrate reproducible administration of effective doses of cell therapy prevents approval for use by government and other regulatory agencies such as the Food and Drug Administration.

Additional challenges are presented when treating neurodegenerative diseases and conditions that are disseminated over a large area of a body, tissue, or organ, such as the entire nervous system rather than a single localized area. For example, in ALS, neurodegeneration involves slow death of motor neurons along the entire spinal cord as well as those neurons in motor cortex. Likewise, in most lysosomal diseases, neuronal destruction involves most regions of the brain and spinal cord. Alzheimer's disease involves most of the cerebrum. Even in more localized neurodegenerative diseases such as Parkinson's and Huntington's, the affected area of striatum is quite large, much larger than the grafting area that can be surgically reached. Thus, cell therapeutics for neurodegenerative diseases are expected to require wider grafting procedures.

There is, therefore, a need for improved methods of treating neurodegenerative conditions. There is also a need for improved methods of culturing and transplanting human neural stem cells and human neural progenitors that once grafted overcome all of the previously seen limitations and provide functional benefit. Thus, this method of treating neurodegenerative conditions, in vivo, generates robust neuronal differentiation, permits long-term neuronal survival under various degenerative conditions and maturation into therapeutically relevant subpopulations of neurons in adult tissues that lack developmental cues, and provides wide therapeutic range than the location of the cells themselves.

SUMMARY

The disclosed methods include methods for treating neurodegenerative conditions. In particular, the disclosed methods include transplanting into a subject in need thereof NSCs, neural progenitors, or neural precursors that have been expanded in vitro such that the cells can ameliorate the neurodegenerative condition. In an embodiment, the disclosed methods include identifying, isolating, expanding, and preparing the donor cells to be used as treatment of the neurodegenerative condition. The donor cells to be transplanted can be selected to correspond to the elements or lack thereof that contribute to the condition, its symptoms and/or its effects.

The cells of the disclosed methods include cells that, upon transplantation, generate an amount of neurons sufficient to integrate within the neuronal infrastructure to ameliorate a disease state or condition. In an embodiment, the disclosed methods include treating neurodegenerative diseases or conditions by transplanting multipotential neural progenitors or neural stem cells isolated from the central nervous system of a mammal and that have been expanded in vitro. For example, transplantation of the expanded neural stem cells can be used to improve ambulatory function in a subject suffering from various forms of myelopathy with symptoms of spasticity, rigidity, seizures, paralysis or any other hyperactivity of muscles.

A method of treatment can include supplying to an injured neural area, via transplantation, a suitable number of NSCs which can differentiate into a sufficient number of GABA-producing neurons and/or glycine-producing neurons to attenuate defective neural circuits, including hyperactive neural circuits.

In an embodiment, the disclosed methods include restoring motor function in a motor neuron disease. A suitable number or a therapeutically effective amount of NSCs or neural progenitors which are capable of differentiating into motor neurons can be provided to at least one area of neurodegeneration, such as a degenerative spinal cord, to restore motor function. The NSCs exert their therapeutic effect by replacing degenerated neuromuscular junctions.

In conjunction or alternatively, the NSCs exert their therapeutic effect by expressing and releasing trophic molecules which protect the neurons of the degenerating tissue so that more of them survive for longer period of time. NSC-derived neurons can be prompted to project into ventral roots and innervate muscle where the NSCs engage in extensive reciprocal connections with host motor neurons in subjects with degenerative motor neuron disease. Therefore, in an embodiment, NSCs from human fetal spinal cord can be grafted into the lumbar cord where these cells can undergo differentiation into neurons that form synaptic contacts with host neurons and express and release motor neuron growth factors.

In an embodiment, the disclosed methods include providing neural stem cells or neural progenitors that integrate with the host tissue and provide one or more growth factors to the host neurons thereby protecting them from degenerative influences present in the tissue. The methods include introducing a sufficient number of NSCs or neural progenitors to an area of a spinal cord such that an effective amount of at least one growth factor is secreted by the NSCs.

In an embodiment, the disclosed methods include providing a method for using animal models in the preclinical evaluation of stem cells for cell replacement in neurodegenerative conditions.

In an embodiment, the disclosed methods include increasing differentiation efficiency of transplanted NSCs into neurons. The method includes expanding highly enriched NSCs or neural progenitors in their undifferentiated state so that, upon transplantation, a sufficient number such as 20% of the cells in the graft adopts a neuronal fate.

In an embodiment, the disclosed methods include increasing the number of differentiated cells without increasing the number of NSCs or neural progenitors to be transplanted. In an embodiment, the method includes preparing the expanded donor population in such a way that, once transplanted, the NSCs or neural progenitors continue to divide in vivo as many as ten times and without generating a tumor, thereby, effectively increasing the total number of delivered cells.

The cells of the disclosed methods can be isolated or obtained from fetal, neonatal, juvenile, adult, or post-mortem tissues of a mammal. The cells of the disclosed methods can be isolated or obtained from the central nervous system, blood, or any other suitable source of stem cells that differentiate into neurons. The cells can also be obtained from embryonic stem cells. For instance, in an embodiment, the cells include neuroepithelial cells isolated from the developing fetal spinal cord. In certain instances, the neural precursor cells can be neural progenitors isolated from specific subregions of the central nervous system.

According to the disclosed methods the neural stem cells are expanded in culture. In an embodiment, the neural precursor cells can be multipotential NSCs capable of expansion in culture and of generating both neurons and glia upon differentiation.

The cells can be either undifferentiated, pre-differentiated or fully differentiated in vitro at the time of transplantation. In an embodiment the cells are induced to differentiate into neural lineage. The cells of the disclosed methods can undergo neuronal differentiation in situ in the presence of pro-inflammatory cytokines and other environmental factors existing in an injured tissue.

Using the present methods, neural circuits can be treated by transplanting or introducing the cells into appropriate regions for amelioration of the disease, disorder, or condition. Generally, transplantation occurs into nervous tissue or non-neural tissues that support survival of the grafted cells. NSC grafts employed in the disclosed methods survive well in a neurodegenerative environment where the NSCs can exert powerful clinical effects in the form of delaying the onset and progression of neurodegenerative conditions or disease.

In some instances, transplantation can occur into remote areas of the body and the cells can migrate to their intended target. Accordingly, the disclosed methods can also include partial grafting of human NSCs. As used herein, the term "partial grafting" can refer to the implantation of expanded NSCs in only a portion of an area or less than an entire area of neurodegeneration. For example, partial grafting of human NSCs into the lumbar segments of spinal cord. At least a portion of the effects of NSCs on degenerating motor neurons include delivery of neurotrophins and trophic cytokines to degenerating host motor neurons via classical cellular mechanisms. To this end, NSCs undergoing partial grafting into the lumbar segments of spinal cord using the disclosed methods have been shown in a transgenic animal model of motor neuron disease to survive, undergo extensive neuronal differentiation, promote motor neuron survival and function in the immediate area of transplantation as well as areas remote from the area of transplantation.

Accordingly, the disclosed methods provide a method of treating spasticity, rigidity, or muscular hyperactivity conditions. The method includes isolating at least one neural stem cell from a mammal and expanding in vitro the neural stem cell to an expanded population. The method also includes concentrating the expanded population and introducing a therapeutically effective amount of the expanded population to at least one area of a recipient spinal cord. At least 20% of the expanded population is capable of generating neurons in the recipient spinal cord.

In an embodiment, the conditions derive from traumatic spinal cord injury, ischemic spinal cord injury, traumatic brain injury, stroke, multiple sclerosis, cerebral palsy, epilepsy, Huntington's disease, amyotropic lateral sclerosis, chronic ischemia, hereditary conditions, or any combination thereof.

In an embodiment, the neural stem cell is isolated from a source selected from the group consisting of a central nervous system, a peripheral nervous system, bone marrow, peripheral blood, umbilical cord blood and at least one embryo.

In an embodiment, the mammal is a developing mammal.

In an embodiment, the gestational age of the developing mammal is between about 6.5 to about 20 weeks.

In an embodiment, the neural stem cell is isolated from a human fetal spinal cord.

In an embodiment, expanding the neural stem cell includes culturing the neural stem cell in the absence of serum.

In an embodiment, expanding the neural stem cell includes exposing the neural stem cell to at least one growth factor.

In an embodiment, the growth factor is selected from the group consisting of bFGF, EGF, TGF-alpha, aFGF and combinations thereof.

In an embodiment, the therapeutically effective amount of the expanded population is capable of generating at least 1,000 GABA-producing neurons in vivo.

In an embodiment, the therapeutically effective amount of the expanded population is capable of generating at least 1,000 glycine-producing neurons in vivo.

In an embodiment, at least 40% of the expanded population is capable of generating neurons in the spinal cord.

In an embodiment, introducing the therapeutically effective amount of the expanded population includes injecting at least a portion of the therapeutically effective amount into a plurality of areas of the recipient spinal cord.

In an embodiment, at least 30% of the expanded population is capable of differentiating into neurons in vitro.

In another embodiment a neural stem cell is provided. The neural stem cell is capable of treating spasticity, rigidity or muscular hyperactivity conditions. The neural stem cell is isolated from a mammal and expanded in vitro to an expanded population. The expanded population including the stem cell is concentrated and a therapeutically effective amount of the expanded population is introduced to at least one area of a recipient spinal cord. At least 20% of the expanded population is capable of generating neurons in the recipient spinal cord.

In another embodiment of the disclosed methods, a method of treating chronic pain is provided. The method includes isolating at least one neural stem cell from a mammal and expanding in vitro the neural stem cell to an expanded population. The method also includes concentrating the expanded population and introducing a therapeutically effective amount of the expanded population to at least one area of a recipient spinal cord. At least 20% of the expanded population is capable of generating neurons in the recipient spinal cord.

In an embodiment, the chronic pain derives from traumatic spinal cord injury, ischemic spinal cord injury, traumatic brain injury, stroke, multiple sclerosis, cerebral palsy, epilepsy, Huntington's disease, amyotropic lateral sclerosis, chronic ischemia, hereditary conditions, or any combination thereof.

In an embodiment, the therapeutically effective amount of the expanded population is capable of generating at least 1,000 GABA-producing neurons.

In an embodiment, the therapeutically effective amount of the expanded population is capable of generating at least 1,000 glycine-producing neurons.

In an embodiment, at least 40% of the expanded population is capable of generating neurons in the spinal cord.

In an embodiment, introducing the therapeutically effective amount of the expanded population includes injecting at least a portion of the therapeutically effective amount into a plurality of areas of the recipient spinal cord.

In an embodiment, the areas include doral horn.

In an embodiment, the areas include intrathecal space.

In a further embodiment a neural stem cell is provided. The neural stem cell is capable of treating chronic pain. The neural stem cell is isolated from a mammal and expanded in vitro to an expanded population. The expanded population including the stem cell is concentrated and a therapeutically effective amount of the expanded population is introduced to at least one area of a recipient spinal cord. At least 20% of the expanded population is capable of generating neurons in the recipient spinal cord.

In another embodiment of the disclosed methods, a method of treating motor neuron degeneration is provided. The method includes isolating at least one neural stem cell from a mammal and expanding in vitro the neural stem cell to an expanded population. The method also includes concentrating the expanded population and introducing a therapeutically effective amount of the expanded population to at least one area of a recipient spinal cord. At least 20% of the expanded population is capable of generating neurons in the recipient spinal cord.

In an embodiment, the motor neuron degeneration derives from traumatic spinal cord injury, ischemic spinal cord injury, traumatic brain injury, stroke, multiple sclerosis, cerebral palsy, epilepsy, Huntington's disease, amyotropic lateral sclerosis, chronic ischemia, hereditary conditions, or any combination thereof.

In an embodiment, the method includes isolating the neural stem cell from an area rich in at least one neuronal subtype, wherein the neuronal subtype produces a growth factor effective in ameliorating the motor deficit.

In an embodiment, the expanded population includes an amount of neural stem cells capable of differentiating into neurons sufficient to secrete a therapeutically effective amount of at least one growth factor.

In an embodiment, the method includes isolating the neural stem cell from an area rich in motor neurons.

In a further embodiment a neural stem cell capable of treating syringomyelia is provided. The neural stem cell is isolated from a mammal and expanded in vitro to an expanded population. The expanded population including the stem cell is concentrated and a therapeutically effective amount of the expanded population is introduced to at least one area of a recipient spinal cord. At least 20% of the expanded population is capable of generating neurons in the recipient spinal cord.

In another embodiment of the disclosed methods, a method of treating syringomyelia is provided. The method includes isolating at least one neural stem cell from a mammal and expanding in vitro the neural stem cell to an expanded population. The method also includes concentrating the expanded population and introducing a therapeutically effective amount of the expanded population to a syrinx of a recipient spinal cord. At least 20% of the expanded population is capable of generating neurons in the syrinx of the recipient spinal cord.

In an embodiment, the syringomyelia derives from traumatic spinal cord injury, ischemic spinal cord injury, traumatic brain injury, stroke, multiple sclerosis, cerebral palsy, epilepsy, Huntington's disease, amyotropic lateral sclerosis, chronic ischemia, hereditary conditions, or any combination thereof.

In an embodiment, the method includes isolating the neural stem cell from an area rich in at least one neuronal subtype, wherein the neuronal subtype produces a growth factor effective in ameliorating the syringomyelia.

In an embodiment, includes isolating the neural stem cell from an area rich in motor neurons.

In an embodiment, the expanded population includes an amount of neural stem cells capable of differentiating into neurons sufficient to secrete a therapeutically effective amount of at least one growth factor.

In an embodiment, the therapeutically effective amount of the expanded population is capable of generating at least 1,000 neurons.

In an embodiment, at least 100,000 neural stem cells of the expanded population are introduced to the syrinx of the recipient spinal cord.

In yet a further embodiment, a neural stem cell capable of treating syringomyelia is provided The neural stem cell is isolated from a mammal and expanded in vitro to an expanded population. The expanded population including the stem cell is concentrated and a therapeutically effective amount of the expanded population is introduced to a syrinx of a recipient spinal cord. At least 20% of the expanded population is capable of generating neurons in syrinx the recipient spinal cord.

In an additional embodiment of the disclosed methods, a method of expanding in vitro at least one neural stem cell to an expanded population of neural stem cells is provided. Each neural stem cell expansion exceeds thirty cell doublings without differentiating. The method includes dissociating neural stem cells from central nervous system tissue and providing at least one extracellular protein to a culture vessel. The extracellular protein includes at least about 10 μg/mL of poly-D-lysine and about 1 mg/ml fibronectin. The method also includes culturing the dissociated neural stem cells in the culture vessel in the absence of serum and adding to the culture vessel at least one growth factor. The growth factor is selected from the group consisting of bFGF, EGF, TGF-alpha, aFGF and combinations thereof. The method further includes passaging the cultured cells prior to confluence.

In an embodiment, the expanded neural stem cells are capable of differentiating into neurons.

In an embodiment, expanding the neural stem cell includes adding fibronectin to culture medium as a soluble factor.

In an embodiment, dissociating the cells and passaging the cells includes enzymatic dissociation.

In an embodiment, the enzymatic dissociation includes treating the cells with trypsin.

In an embodiment, a therapeutically effective amount of the expanded population is introduced to at least one area of a recipient nervous system to treat a neurodegenerative condition.

It is therefore an advantage of the disclosed methods over existing pharmacological strategies to provide a method of facilitating the ability of the transplanted NSCs to secrete trophic molecules which can be delivered to degenerating motor neurons under conditions of optimal bioavailability.

Yet another advantage of the present invention is to provide a method of culturing and expanding NSCs from human fetal spinal cord to facilitate the successful engraftment of the NSCs into the lumbar cord.

A further advantage of the disclosed methods includes providing a method of achieving a higher proportion of neuronal differentiation of a population of NSCs.

Another advantage of the disclosed method includes achieving clinical effects from partial grafting of NSCs.

Additional features and advantages of the disclosed methods are described in, and will be apparent from, the following Detailed Description of the Invention and the figures.

BRIEF DESCRIPTION OF THE FIGURES

FIG. 3. Characterization of differentiated cultures obtained from expanded human spinal stem cells. The expanded cells of passage 15-16 were differentiated for approximately 14 days in culture, fixed, and stained with various neuron-specific antibodies. (A) Tau and MAP2; (B) Type 3 beta tubulin; (C) GABA; (D) Acetylcholine transferase.

Figure 1:
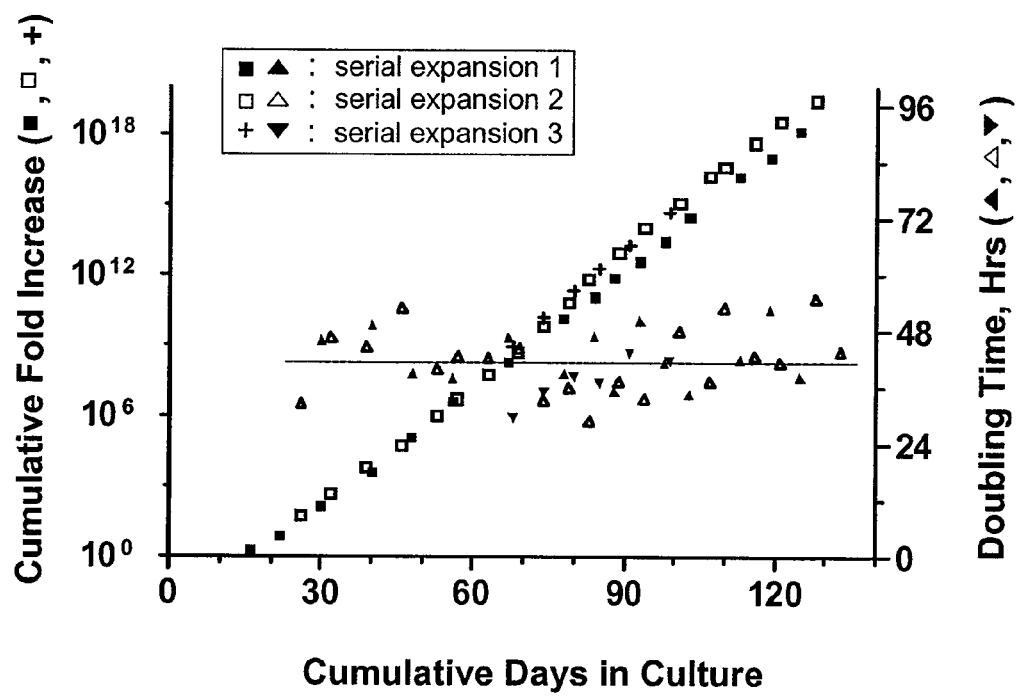
FIG. 1. Expansion of human spinal stem cells. A human spinal progenitor (a.k.a. NSC) line was isolated from a 7-8 week old post-mortem fetal spinal cord tissue and serially passaged for about 130 days of net culture period. At each passage, the cell number recovered at harvest was divided by the initial cell number at plating to obtain the fold-increase in cell number. Cumulative fold-increase (left Y axis) was obtained by multiplying the fold-increase at each passage. Doubling time (right Y axis) of the cells at each passage was calculated by dividing the fold-increase in cell number by the each culture period (X axis). This process was repeated three times (serial expansion 1, 2, and 3).

A-B. Panel A is a Kaplan-Meier plot showing a significant separation between experimental and control animals throughout the course of observation (P=0.0003). Panel B shows a separation in the two principal measures of muscle weakness (BBB and incline plane scores) between the two groups (P=0.00168 and 0.00125, respectively).

C-E. End-point analysis of survival (C), time-to-disease-onset (D) and motor neuron numbers (E) in experimental and control rats. Panel C shows a significant 11-day difference in life span between the two groups (P=0.0005). Panel D shows a significant 7-day difference in time-to-disease-onset between the two groups (P=0.0001). Panel E shows a difference of 3, 212 cells in the lumbar protuberance between live and dead NSC groups (P=0.01). Inset at the bottom of (E) illustrates the difference in motor neuron survival between a representative experimental (up) and control (down) rat at 128 days of age; arrows indicate the lateral motor neuron group. Size bars: 150 μm.

DETAILED DESCRIPTION

The disclosed methods are related to treating neurodegenerative conditions. In particular, the disclosed methods include methods of preparing neural stem cells for transplantation into a subject in need thereof. Preparing the cells for transplantation can include expanding in vitro a specific population of cells to a level sufficient for commercial use as a treatment for neurodegenerative conditions. In an embodiment, the method of treatment of a degenerated or an injured neural area includes supplying to the area an effective number of neural stem cells sufficient to ameliorate the neurodegenerative condition.

As used herein, a neurodegenerative condition can include any Disease or disorder or symptoms or causes or effects thereof involving the damage or deterioration of neurons. Neurodegenerative conditions can include, but are not limited to, Alexander Disease, Alper's Disease, Alzheimer Disease, Amyotrophic Lateral Sclerosis, Ataxia Telangiectasia, Canavan Disease, Cockayne Syndrome, Corticobasal Degeneration, Creutzfeldt-Jakob Disease, Huntington Disease, Kennedy's Disease, Krabbe Disease, Lewy Body Dementia, Machado-Joseph Disease, Multiple Sclerosis, Parkinson Disease, Pelizaeus-Merzbacher Disease, Niemann-Pick's Disease, Primary Lateral Sclerosis, Refsum's Disease, Sandhoff Disease, Schilder's Disease, Steele-Richardson-Olszewski Disease, Tabes Dorsalis or any other condition associated with damaged neurons. Other neurodegenerative conditions can include or be caused by traumatic spinal cord injury, ischemic spinal cord injury, stroke, traumatic brain injury, and hereditary conditions.

The disclosed methods include the use of NSCs to ameliorate a neurodegenerative condition. As used herein, the term, "NSCs" can also refer to neural or neuronal progenitors, or neuroepithelial precursors. NSCs can be functionally defined according to their capacity to differentiate into each of the three major cell types of the CNS: neurons, astrocytes, and oligodendrocytes.

In an embodiment, the NSCs are multipotential such that each cell has the capacity to differentiate into a neuron, astrocyte or oligodendrocyte. In an embodiment, the NSCs are bipotential such that each cell has the capacity to differentiate into two of the three cell types of the CNS. In an embodiment, the NSCs include at least bipotential cells generating both neurons and astrocytes in vitro and include at least unipotential cells generating neurons in vivo.

Growth conditions can influence the differentiation direction of the cells toward one cell type or another, indicating that the cells are not committed toward a single lineage. In culture conditions that favor neuronal differentiation, cells, particularly from human CNS, are largely bipotential for neurons and astrocytes and differentiation into oligodendrocytes is minimal. Thus, the differentiated cell cultures of the disclosed methods may give rise to neurons and astrocytes. In an embodiment, the ratio of neurons to astrocytes can approach a 50:50 ratio.

The disclosed methods include obtaining NSCs residing in regions of a mammalian CNS such as the neuroepithelium. Other CNS regions from which NSCs can be isolated include the ventricular and subventricular zones of the CNS and other CNS regions which include mitotic precursors as well as post-mitotic neurons. In an embodiment, the disclosed methods can employ NSCs residing in regions of a developing mammalian CNS.

In an embodiment, the NSCs are obtained from an area which is naturally neurogenic for a desired population of neurons. The desired population of cells may include the cells of a specific neuronal phenotype which can replace or supplement such phenotype lost or inactive in a neurological condition.

A variety of different neuronal subtypes, including those useful for treatment of specific neurodegenerative diseases or conditions can be obtained by isolating NSCs from different areas or regions of the CNS and across different gestational ages during fetal development. NSCs isolated from different areas or regions of the CNS and across different gestational ages are used for optimal expansion and neuronal differentiation capacity. One of the hallmarks of the mammalian CNS is the diversity of neuronal subtypes. A single population of NSCs, for example, may spontaneously generate only a few distinct neuronal subtypes in culture. Furthermore, the cells from a particular fetal gestational age may establish the physiological relevance of the cultured cells.

In an embodiment of the disclosed methods, the cells to be transplanted into subjects are derived from the human fetal counterpart of the injured neural area. In an embodiment, NSCs are isolated from human fetal CNS regions at gestational ages of between about 6.5 to about 20 weeks. In an embodiment, cells from a fetal spinal cord are isolated at a gestational age of about 7 to about 9 weeks. It should be appreciated that the proportion of the isolatable neural stem cell population can vary with the age of the donor. Expansion capacity of the cell populations can also vary with the age of the donor. Such regional and temporal specificity of NSCs indicates that NSCs behave as fate-restricted progenitors and not as blank cells or a single population of cells.

The proportion of the population in vitro including GABA-producing neurons is generally constant at about 5-10%.

The NSCs of the ventral midbrain, for example, are distinct from the NSCs obtained from the spinal cord at the same gestational stage. In particular, the NSCs from the ventral midbrain exclusively give rise to tyrosine-hydroxylase-expressing dopaminergic neurons, whereas NSCs from the spinal cord exclusively generate acetylcholine-producing cholinergic neurons. Both cell types, however, simultaneously generate the more ubiquitous glutamate- and GABA-producing neurons. Therefore, in an embodiment, the disclosed methods include obtaining NSCs from the ventral midbrain to treat conditions ameliorated or attenuated, at least in part, by the implantation of tyrosine-hydroxylase-expressing dopaminergic neurons. The disclosed methods further include obtaining NSCs from the spinal cord to treat neurodegenerative conditions ameliorated or attenuated, at least in part, by the implantation of acetylcholine-producing cholinergic neurons.

Thus, for treatment of movement disorders such as Parkinson's disease which is characterized by the loss of dopaminergic neurons, an embodiment of the disclosed methods includes the use of NSCs derived from an area such as the ventral midbrain in which neurogenesis of dopaminergic neurons is substantial. In addition, the NSCs can be obtained at a gestational age of human fetal development during which neurogenesis of dopaminergic neurons is substantial. Accordingly, in an embodiment, the disclosed methods include obtaining NSCs from the ventral midbrain derived at a gestational age of about 7 to about 9 weeks to treat movement disorders.

For treating motor neuron diseases such as amyotrophic lateral sclerosis or flaccid paraplegia resulting from loss of ventral motor-neurons, an embodiment of the disclosed methods includes the use of NSCs derived from an area such as the spinal cord in which neurogenesis of ventral motor-neurons is substantial and obtained at a gestational age of human fetal development during which neurogenesis of ventral motor-neurons is substantial. Accordingly, in an embodiment, NSCs are isolated from the spinal cord at a gestational age of about 7 to about 9 weeks to treat motor neuron diseases.

It should be appreciated, however, that, in some cases, the limits of such regional specificity are fairly broad for practical purposes. Thus, NSCs from various areas of the spinal cord such as cervical, thoracic, lumbar, and sacral segments can be used interchangeably to be implanted and to treat locations other than the corresponding origin of the NSCs. For example, NSCs derived from cervical spinal cord can be used to treat spasticity and/or rigidity by transplanting the cells into the lumbar segments of a patient.

NSCs can also be isolated from post-natal and adult tissues. NSCs derived from post-natal and adult tissues are quantitatively equivalent with respect to their capacity to differentiate into neurons and glia, as well as in their growth and differentiation characteristics. However, the efficiency of in vitro isolation of NSCs from various post-natal and adult CNS can be much lower than isolation of NSCs from fetal tissues which harbor a more abundant population of NSCs. Nevertheless, as with fetal-derived NSCs, the disclosed methods enable at least about 30% of NSCs derived from neonatal and adult sources to differentiate into neurons in vitro. Thus, post-natal and adult tissues can be used as described above in the case of fetal-derived NSCs, but the use of fetal tissues is preferred.

Various neuronal subtypes can be obtained from manipulation of embryonic stem cells expanded in culture. Thus, specific neuronal subtypes, based on the disclosed methods, can be isolated and purified from other irrelevant or unwanted cells to improve the result, as needed, and can be used for treatment of the same neurodegenerative conditions.

The NSCs in the disclosed methods can be derived from one site and transplanted to another site within the same subject as an autograft. Furthermore, the NSCs in the disclosed methods can be derived from a genetically identical donor and transplanted as an isograft. Still further, the NSCs in the disclosed methods can be derived from a genetically non-identical member of the same species and transplanted as an allograft. Alternatively, NSCs can be derived from non-human origin and transplanted as a xenograft. With the development of powerful immunosuppressants, allograft and xenograft of non-human neural precursors, such as neural precursors of porcine origin, can be grafted into human subjects.

A sample tissue can be dissociated by any standard method. In an embodiment, tissue is dissociated by gentle mechanical trituration using a pipet and a divalent cation-free saline buffer to form a suspension of dissociated cells. Sufficient dissociation to obtain largely single cells is desired to avoid excessive local cell density.

For successful commercial application of NSCs, maintaining robust and consistent cultures that have stable expansion and differentiation capacities through many successive passages is desirable. As described above, the culture methods can be optimized to achieve long-term, stable expansion of an individual cell line of NSCs from different areas and ages of CNS development while maintaining their distinct progenitor properties.

To this end, it has been surprisingly found that promoting the adhesion of NSCs (NSCs) to a substrate contributes to accelerating the mitotic rate of NSC or progenitor cells, thereby, providing significant enhancement of a more robust culture of NSC or progenitor cells. In particular, in addition to avoiding excessive local cell density and maintaining mitogen concentrations, it has been found that the concentrations of extracellular matrix proteins affect the long-term mitotic and differentiation capacity of NSCs. The extracellular matrix proteins can include poly-D-lysine, poly-L-lysine, poly-D-ornithine, poly-L-ornithine, fibronectin and combinations thereof. Other extracellular matrix proteins can include various isotypes, fragments, recombinant forms, or synthetic mimetics of fibronectin, lamin, collagen, and their combinations. Alternatively, or in addition, it should be appreciated that the disclosed methods can include any other suitable substance that is able to promote effective cell adhesion so that each individual cell is adhered to the culture substrate during the entire duration of the culture without being cytotoxic or retarding the cell division.

Although extracellular matrix proteins can be effective in promoting cell adhesion, different amino acid polymers, such as poly-L/D-ornithine or poly-L/D-lysine, can be toxic to the cells at certain concentrations for each individual cell line. The duration of incubation can also affect the final amount of the polymer deposited on the dish surface affecting the viability of the cells. For the NSCs employed in the disclosed methods, concentrations of polymer can be within a range of between about 0.1 µg/mL and about 1 mg/mL. In an embodiment, 100 µg/ml of poly-D-lysine is dissolved in 0.01M HEPES buffer or water at neutral pH and applied to a culture vessel. The culture vessel is incubated for 1 hour at room temperature. The culture vessel is then thoroughly rinsed with water and dried prior to use.

The disclosed methods can also include double-coating the culture vessels with an extracellular matrix protein. In an embodiment, the culture vessel is treated with fibronectin or a fibronectin derivative following the application of poly-L/D-ornithine or poly-L/D-lysine described above. In an embodiment, fibronectin protein prepared from human plasma is used. It should be appreciated, however, that any other suitable form or source of fibronectin protein can be used such as porcine or bovine fibronectin, recombinant fibronectin, fragments of fibronectin proteins, synthetic peptides, and other chemical mimetics of fibronectin. In an embodiment, between about 0.1 µg/mL to about 1 mg/mL of fibronectin can be applied.

In an embodiment including the expansion of NSCs from human spinal cord, the culture vessel is treated with 100 µg/mL of poly-D-lysine for a period sufficient to allow the extracellular protein to bind to and coat the culture vessel. Such a time period can be for about five minutes to about three hours. The culture vessel can be subsequently washed with water. After air-drying the culture vessel, the vessel can be treated with about 25 mg/ml fibronectin for approximately five minutes to several hours at room temperature or about 1 mg/ml fibronectin for approximately 1 hour to several days at 37° C. Subsequently, the fibronectin can be removed and the culture vessel can be washed at least once or stored in PBS until use.

Alternatively, fibronectin can be added into the growth medium as a soluble factor supplied directly to the cells. In this embodiment, NSCs can be expanded by adding 1 µg/mL of fibronectin into the growth medium in addition to, or instead of, treatment of the culture vessels with fibronectin. Supplying the attachment protein into the growth medium as a soluble factor at the time of cell plating is particularly advantageous for large commercial-scale culturing of NSCs due to the relatively short shelf-life of fibronectin-coated vessels. This method is also useful for manufacturing a neural stem cell line requiring substantially exact conditions and reproducibility such as required under cGMP protocols and for manufacturing the neural stem cell line for therapeutic use.

In an embodiment, the isolated NSCs are added to the culture vessel at a density of about 1,000 to about 20,000 cells per square cm. Such a density contributes to even dispersion and adhesion of individual cells in the culture vessel, avoiding localized concentrations of cells, to enriched the culture for NSCs.

In an embodiment, NSCs are expanded in the absence of serum. In an embodiment, the NSCs are cultured in a defined, serum-free medium to avoid exposure of the NSCs to concentrations of serum sufficient to destabilize the mitotic and differentiation capacity of NSC. In addition, exposure of the NSCs to certain growth factors such as leukemia inhibitory factor (LIF) or ciliary neurotrophic factor (CNTF) can also destabilize NSCs and should be avoided.

Mitogens can be added to the culture at any stage of the culture process to enhance the growth of the NSCs. Mitogens can include basic fibroblast growth factor (bFGF), acidic fibroblast growth factor (aFGF), epidermal growth factor (EGF), transforming growth factor-alpha (TGFa), and combinations thereof.

NSCs of the disclosed methods can be grown and expanded in at least two different culture forms. One form of culture includes an aggregated form, commonly referred to as a clustered, aggregated form referred to as a suspension culture. Another form of culture includes a dispersed, non-aggregated form referred to as an adhesion culture.

In a dispersed adherent culture of the NSCs of the disclosed methods, the cells form a monolayer in which individual cells initially contact the culture substrate directly. Eventually, after a period of incubation, the cells can sporadically form clusters, wherein at least one additional layer of cells is formed on the bottom layer, even as the cells in the bottom layer are individually adhered to the substrate. Such clustering especially occurs when the culture is inoculated at high cell density or allowed to reach high cell density, which, in an embodiment, is minimized for optimal expansion of NSCs or progenitor cells or for optimal maintenance of the multipotential capacity of the NSCs. In the dispersed adherent culture of an embodiment of the disclosed methods, human NSCs are enabled to divide in less than about four days per cell division.

Another distinctive characteristic of the dispersed adherent culture is that the NSCs of the disclosed methods divide to generate daughter cells, each retaining their multipotential capacity. In an embodiment, the dispersed adherent culture of NSCs of the disclosed methods includes an expansion capacity of at least 20 cell doublings in the absence of substantial differentiation. Most NSCs can be expanded beyond at least 50 cell doublings before losing their neurogenic potential. In an embodiment, the NSCs expanded in the dispersed adherent culture of the disclosed methods demonstrate enhanced neuronal differentiation, giving rise, in an embodiment, to at least about 30% neuronal differentiation. In many cases, at least 50% of NSCs differentiate into neurons. Although the dispersed, adherent form of culture is a more preferred form of culture, the different culture methods may allow isolation of innately distinct cell populations with differing differentiation potentials either in vitro or in vivo.

The present method also allows clonal isolation of NSCs from a variety of sources without genetic modification or inclusion of feeder cells. Thus, a very low number, preferably less than 1000 cells per square centimeter of cells, may be seeded in a cell culture dish prepared as described above.

A few days following seeding of the NSCs, the cells can form well-isolated colonies. The colonies may be grown to a desired size such as at least about 250 to about 2000 cells. In an embodiment, at least one colony of cells is manually picked and inoculated individually to a fresh cell culture dish such as a multi-well plate.

Isolated clonal populations may be expanded by serial passaging and used to establish multiple neural stem cell lines. Many such clonal cell lines have been isolated from various areas of the human CNS including spinal cord, midbrain, and hindbrain. Clonal cell lines are useful to enrich for a particular cell phenotype such as a higher proportion of neuronal subtypes. For example, clonal cell lines enriched for tyrosine hydroxylase-expressing dopaminergic neurons, GABAergic neurons, cholinergic neurons and neurons of other specific phenotypes can be isolated with the disclosed methods.

In an embodiment, either a polyclonal or a monoclonal neural stem cell line can be induced to be further enriched for a particular subtype of neurons. A number of growth factors, chemicals, and natural substances have been screened to identify effective inducers of particular neurons such as tyrosine hydroxylase-expressing dopaminergic neurons and acetylcholine-producing cholinergic neurons from NSCs of midbrain or spinal cord. The factor or chemical or combination thereof can be introduced during the mitotic phase and/or the differentiation phase of the NSCs. In an embodiment, a neural stem cell line for a dopaminergic phenotype is further enriched as a donor population to treat Parkinson's disease.

Various neuronal subtypes can be obtained from isolation of stem cells having a desired differentiation pattern in vitro. In vitro results can be substantially reproduced in vivo. This means that the potential efficacy of the stem cells in vivo can be predicted by the differentiation pattern of the stem cells in vitro. Upon injection into live post-natal subjects, NSCs, in either an undifferentiated or pre-differentiated state, produces to a large extent an in vivo differentiation pattern observed in vitro. Thus, NSC giving rise to tyrosine hydroxylase-producing neurons in vitro also generate tyrosine hydroxylase-producing neurons in vivo. Conversely, NSCs not giving rise to tyrosine hydroxylase-producing neurons constitutively in vitro do not produce tyrosine hydroxylase-producing neurons in vivo.

However, differentiation cues present in vitro are limited compared to those in vivo. Thus, a substantial fraction of the differentiated neurons may not express a major neurotransmitter phenotype. Additional cues such as signals from afferent or efferent neurons, or agents mimicking such natural signals can be used to re-configure the differentiated phenotypes, either during the mitotic stage of NSCs or during their differentiation. NSCs have the ability to respond to cues present in vivo as well as in vitro. Thus, once grafted into ischemia-injured spinal cord, the spinal NSCs generate a substantially higher proportion of GABA-producing neurons than in vitro. Thus, NSCs are plastic. Such plastic nature of NSCs is a characteristic of their multipotentiality and, as such, this plasticity can be used to identify phenotype-inducing agents and conditions which can be further combined with an NSC population to re-direct its properties.

In an embodiment, such re-programming includes treating NSCs from a spinal cord tissue to obtain enhanced expression of motor neuron phenotypes. The treatment conditions include co-culturing NSCs or their differentiated cells with various muscle cells or peripheral nervous system-derived cells such as neural crest cells or ganglionic neurons. NSCs can also be treated with cocktails of molecules known to be expressed and produced in motor neurons or in the spinal cord to enhance NSC expression of motor neuron phenotypes.

To induce enhanced NSC expression of the dopaminergic phenotype of human midbrain, NSCs are treated with molecules such as lithium, GDNF, BDNF, pleiotrophin, erythropoietin, conditioned media from cells such as sertoli cells, or any other suitable chemicals or cells obtained by screening or combinations thereof. Such inducement can enable the transplanted NSCs to express and maintain the dopaminergic phenotype in vivo.

In an embodiment, the NSCs of the disclosed methods can include pre-differentiated cells for transplantation. For maximum yield of the cells and for simplicity of the procedure, a confluent culture is harvested for transplantation which comprises primarily a population of undifferentiated cells. It should be appreciated, however, that a minor population of cells just starting to differentiate spontaneously can also exist due to the increased cell density.

In an embodiment, passaging NSCs includes harvesting or detaching the cells from a substrate. In an embodiment, the disclosed methods include harvesting or detaching the cells from a substrate using at least one enzyme. Enzymatic treatment can be avoided when the cell cycle time of the NSCs is short enough to deactivate the mitogen receptors on the cell surface. However, the cell cycle time of human NSCs is much longer than rodent NSCs such that human NSCs are not as sensitive to enzymatic treatment. Thus, in the disclosed methods, enzymatic treatment is used for harvesting NSCs derived from a human. Although the human NSCs can become temporarily refractory to mitogen in the presence of enzymatic treatment, repeated deactivation of the mitogen receptors can lead to a decreased proportion of NSCs.

In an embodiment, upon harvesting of the cells, the cells are concentrated by brief centrifugation. The cells can be further washed and re-suspended in a final, clinically usable solution such as saline, buffered saline, or, alternatively, be re-suspended in a storage or hibernation solution. Alternatively, the cells can be re-suspended in a freezing medium such as media plus dimethylsulfoxide, or any other suitable cryoprotectant, and frozen for storage.

The hibernation solution is formulated to maintain the viability of live cells for a prolonged period of time. In an embodiment, the storage solution can be adapted to be used for shipping live cells in a ready-to-use formulation to a transplantation surgery site for immediate use. Suitable conditions for shipping live cells to a distant site also includes an insulation device that can maintain a stable temperature range between about 0° C. and about 20° C. for at least 24 hours. Live cells stored at between about 0° C. and about 8° C. for about 24 hours to about 48 hours are engraftable for treatment of a disease or condition.

In an embodiment, the cells are concentrated in a solution such as the clinically usable, hibernation or freezing solutions described above. In an embodiment, the cells are concentrated to an appropriate cell density which can be the same or different from the cell density for administration of the cells. In an embodiment, the cell density for administration can vary from about 1,000 cells per microliter to about 1,000,000 cells per microliter depending upon factors such as the site of the injection, the neurodegenerative status of the injection site, the minimum dose necessary for a beneficial effect, and toxicity side-effect considerations. In an embodiment, the disclosed methods include injecting cells at a cell density of about 5,000 to about 50,000 cells per microliter.

The volume of media in which the expanded cells are suspended for delivery to a treatment area can be referred to herein as the injection volume. The injection volume depends upon the injection site and the degenerative state of the tissue. More specifically, the lower limit of the injection volume can be determined by practical liquid handling of viscous suspensions of high cell density as well as the tendency of the cells to cluster. The upper limit of the injection volume can be determined by limits of compression force exerted by the injection volume that are necessary to avoid injuring the host tissue, as well as the practical surgery time.

Low cell survival of donor cells using known methods has necessitated the delivery of a large quantity of cells to a relatively small area in order to attempt effective treatment. Injection volume, however, is hydrostatic pressure exerted on the host tissue and the prolonged injection time associated with high injection volumes exacerbates surgical risk. Additionally, over-injection of donor cells leads to compression and subsequent injury of the host parenchymal tissue. In attempting to compensate for volume constraints, known methods have required preparation of high cell density suspensions for the injections. However, a high cell density promotes tight clustering of the transplanted cells and inhibits cell migration or spreading preventing effective treatment beyond a limited area and compromising seamless integration into the host tissue.

In contrast, as a result of improved survival in vivo of the cells prepared by the disclosed methods, fewer number of cells are needed per injection. In fact, up to three to four times the number of injected cells have been shown to exist after six months from the time of injection demonstrating significant quantitative survival using the disclosed methods. Also, because of the quantitative survival, reproducible administration of desired cell doses can be achieved. Accordingly, in an embodiment, the cells are concentrated to a density of about 1,000 to about 200,000 cells per microliter. In an embodiment, about 5,000 to about 50,000 cells per microliter have been used for effective engraftment. In another embodiment, about 10,000 to 30,000 cells per microliter is used. In an embodiment, the cells can be delivered to a treatment area suspended in an injection volume of less than about 100 microliters per injection site. For example, in the treatment of neurodegenerative conditions of a human subject where multiple injections may be made bilaterally along the spinal tract, an injection volume of 0.1 and about 100 microliters per injection site can be used.

Any suitable device for injecting the cells into a desired area can be employed in the disclosed methods. In an embodiment, a syringe capable of delivering sub-microliter volumes over a time period at a substantially constant flow rate is used. The cells can be loaded into the device through a needle or a flexible tubing or any other suitable transfer device.

In an embodiment, the desired injection site for treatment of a neurodegenerative condition includes at least one area of the spinal cord. In an embodiment, the cells are implanted into at least one specific segment or region of the spinal cord such as the cervical, thoracic or lumbar region of the spinal cord. In the lumbar region, for example, only five pairs of nerve roots traverse the bony canal of vertebrae with each pair of nerve roots exiting the spine at each lumbar level distributed over a wide area. Due to a lower density of nerve roots in the lumbar region of the spinal cord, the lumbar region is particularly well-suited for providing a safe site for injection of cells. In an embodiment, the cells are implanted in the intermediate zone of the spinal cord parenchyma.

In an embodiment, the cells are injected at between about 5 and about 50 sites. In an embodiment, the cells are injected at between about 10 to about 30 sites on each side of the cord. At least two of the sites can be separated by a distance of approximately 100 microns to about 5000 microns. In an embodiment, the distance between injection sites is about 400 to about 600 microns. The distance between injections sites can be determined based on generating substantially uninterrupted and contiguous donor cell presence throughout the spinal segments and based on the average volume of injections demonstrated to achieve about 2-3 month survival in animal models such as rats or pigs. In an embodiment, the cells are injected along both sides of the midline of the spinal cord to span the length of at least several lumbar segments useful for treating a symptom such as spasticity/rigidity or motor neuron survival. The actual number of injections in humans can be extrapolated from results in animal models.

In an embodiment, the target site of injection is the gray matter of the spinal cord. Within the gray matter, the needle tip can be positioned to deposit the NSCs at specific levels of lamina. For instance, to deliver GABA/glycine-producing neurons to treat spasticity/rigidity, the NSCs are delivered to the area encompassing lamina V-VII. Alternatively, the NSCs can be delivered to or near the dorsal horn of the gray matter of various spinal segments, from cervical to lumbar, in order to treat neuropathic pain or chronic pain. Alternatively, the NSCs can be delivered to or near the ventral horn of the gray matter of various spinal segments from cervical to lumbar in order to treat motor neuron diseases such as ALS.

The cells of the disclosed methods can generate large numbers of neurons in vivo. When the NSCs are not overtly pre-differentiated prior to transplant, the NSCs can proliferate up to two to four cell divisions in vivo before differentiating, thereby further increasing the number of effective donor cells. Upon differentiation, the neurons secrete specific neurotransmitters. In addition, the neurons secrete into the milieu surrounding the transplant in vivo growth factors, enzymes and other proteins or substances which are beneficial for different conditions. Accordingly, a variety of conditions can be treated by the disclosed methods because of the ability of the implanted cells to generate large numbers of neurons in vivo and because the neurodegenerative conditions may be caused by or result in missing elements including neuron-derived elements. Therefore, subjects suffering from degeneration of CNS tissues due to lack of such neuron-derived elements, such as growth factors, enzymes and other proteins, can be treated effectively by the disclosed methods.

Conditions responding to growth factors, enzymes and other proteins or substances secreted by the implanted neurons include hereditary lysosomal diseases such as Tay-Sach's disease, Niemann-Pick's disease, Batten's disease, Crabb's disease, ataxia, and others.

In addition, the disclosed methods of treatment include implanting the cells expanded in vitro which can replace damaged or degenerated neurons, provide an inhibitory or stimulatory effect on other neurons, and/or release trophic factors which contribute to the regeneration of neurons.

An embodiment includes supplying additional motor neurons as replacement of damaged or degenerated neurons. For example, the disclosed methods include providing sufficient neural infrastructure within the syrinx of the spinal cord to fill the cavitation. Neural infrastructure is sufficient if it is capable of slowing the enlargement of the syrinx associated with syringomyelia resulting from traumatic spinal injury, hereditary conditions or any other cause. It should be appreciated that providing sufficient neural infrastructure also helps relieve further complications arising from degenerating spinal cord.

Not all NSCs are therapeutic for a given disease. The types of neuronal populations affected in different diseases may be different. Therefore, a therapeutically effective donor population of NSCs contributes to replacing the lost neural element. For example, treatment of spasticity, seizure, movement disorders, and other muscular hyperactivity disorders, can include providing a therapeutically effective amount of cells capable of differentiating into inhibitory neurons producing GABA or glycine. Distinct populations of NSCs can be assessed in vitro by examining the differentiated neuronal phenotype. The in vitro differentiation pattern is then used to predict the efficacy of the cells to produce the appropriate phenotype in vivo, not only in terms of an appropriate neurotransmitter phentoype, but also in terms of an appropriate morphology, migration, and other phenotypic characteristics of neurons.

In an embodiment, NSCs are implanted that are capable of generating the neuronal subtype corresponding to the damaged or destroyed neuronal subtypes associated with the etiology of the symptoms. For example, hyperactivity of excitatory circuits in subjects can be caused by hereditary conditions or neuronal injury from spinal trauma, thoracic/thoracoabdominal aorta surgery, stroke, epilepsy, brain trauma, Huntington's disease, bladder incontinence, hyperactive bowel movement and any other uncontrolled contraction of muscles arising from injury or hereditary conditions. Spasticity, seizures, or other hyperactivity occurs in the brain as opposed to the spinal cord due to a number of different etiological origins. Focal epilepsy, for example, is thought to arise from disregulated hyperactivity due to a lack of GABA exerting tonal control over the circuitry. To this end, disclosed methods include providing inhibitory neurotransmitters such as GABA or glycine in the affected areas by transplantation of in vitro expanded NSCs. In the case of spasticity, seizure, and other hyperactivity, for example, a number of NSCs which are capable of differentiating into inhibitory neurons, such as GABA-producing or glycine-producing neurons, are generated in vivo to be transplanted to attenuate at least one hyperactive neural circuit associated with spasticity, seizure, and other neuronal hyperactivity. The disclosed methods can, therefore, be applied to treat epilepsy and similar conditions of seizures.

The disclosed methods can also be applied to treat paresis, paralysis, spasticity, rigidity or any other motor, speech, or cognitive symptoms arising from cerebral ischemia. Cerebral ischemia can occur as a result of a stroke event in the brain or from a heart attack in which the blood circulation to the brain is interrupted for a significant period of time. It is, thus, analogous to the spinal cord ischemia described above. Some stroke subjects develop seizures of central origin as well as other deficits such as memory loss, paralysis, or paresis. These deficits from cerebral ischemia are also likely due to selective loss of inhibitory interneurons in hippocampus and/or other brain areas. Thus, the disclosed methods can be applied to treat stroke subjects suffering from paresis, paralysis, spasticity, or other motor, speech, and cognitive symptoms.

In the case of paresis, flaccid paraplegia, and other conditions associated with a loss of control of muscle contraction such as those caused by ALS, traumatic spinal cord injury, ischemic injury, or hereditary conditions, the disclosed methods include providing neuronal implantation to exert sufficient trophic influence to slow the loss of motor neurons. In particular, the disclosed methods facilitate the ability of the transplanted NSCs to secrete trophic molecules which can be delivered to degenerating motor neurons under conditions of optimal bioavailability. Such trophic molecules include exocytosed superoxide dismutases such as superoxide dismutase (SOD1), lysosomal enzymes, and non-proteinatious molecules such as cell-produced antioxidants. Other trophic factors secreted by the transplanted cells can include global cell-derived neurotrophic factor (GDNF), brain-derived neurotrophic factor (BDNF), vascular epidermal growth factor (VEGF), pleiotrophin, vascular endothelial growth factor (VEGF), erythropoietin, midkine, insulin, insulin-like growth factor 1 (IGF-1), and insulin-like growth factor 2 (IGF-2) or any other beneficial trophic element.

Another factor that contributes to the ability of the disclosed methods to treat a wide range of neurodegenerative conditions includes the ability of the NSC-differentiated cells to migrate extensively along existing neuronal fibers. Migration of the grafted cells results in global distribution and integration of donor neurons and/or glia and global or dispersed supply of the therapeutic element secreted by such cells.

Wide migration of the cells enables the global and stable delivery of key therapeutic proteins and substances throughout a nervous system and body of a subject in need thereof. Thus, the cells of the disclosed methods are effective delivery vehicles for therapeutic proteins and substances. For such delivery purposes, the disclosed methods include transplanting the cells into various sites within the nervous system including the CNS parenchyma, ventricles, the subdural, intrathecal and epidural spaces, peripheral nervous system sites as well as into areas outside of the nervous system including the gut, muscle, endovascular system, and subcutaneous sites.

Example 1

Expansion of Human Spinal Cord Neural Stem/Progenitor Cells

Spinal cord from at least one donor of gestational age of approximately 7-8.5 weeks is obtained. A single contiguous tissue of the spinal cord is dissociated in $Ca^{++}$ and $Mg^{++}$-free phosphate buffered saline using mechanical trituration. The resulting cell suspension is then seeded into tissue culture plates pre-coated with both poly-L-ornithine or poly-D-lysine and human fibronectin or other extracellular matrix proteins. Tissue culture-treated plates or flasks were incubated with 100 □g/ml poly-D-lysine for 1 hour at room temperature. They were then washed three times with water and dried. They were then incubated with 25 mg/ml for 5 minutes at room temperature. Sometimes, 10 mg/ml fibronectin for 1 hour at room temperature was used. Sometimes, 1 mg/ml fibronectin for 18 hours at 37° C. was used. Culture media consisting of N2 (DMEM/F12 plus insulin, transferrin, selenium, putrescine, and progesterone) was supplemented with human recombinant basic fibroblast growth factor (bFGF). In an embodiment, a range of 0.1 ng/ml-100 ng/ml can be used. In an embodiment, optimally, 10 ng/ml of bFGF is used.

Figure 2:
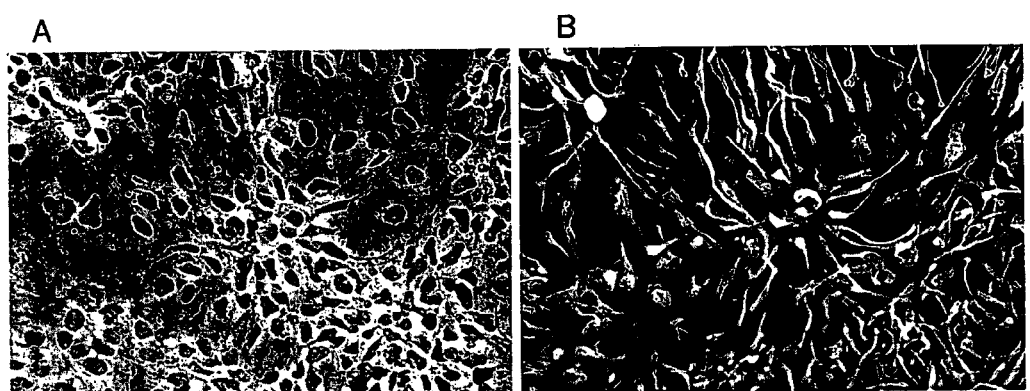
FIG. 2. Morphology of expanded human spinal stem cells. (A) Phase contrast view of a fixed, unstained, expanding culture, 20× objective, (B) Anti-nestin antibody staining.

The resulting initial culture consists of post-mitotic neurons and proliferative NSCs in a monolayer. Subsequently, after approximately five to about twenty days in culture, the dividing, nestin-positive, NSCs dominate the culture over the non-dividing neurons or the slowly-dividing glia. Under these culture conditions, NSCs are selectively favored for expansion. The expanding NSC population is passaged by mild enzymatic treatment, such as using trypsin. The cells are cultured in media free of serum or substantially free of serum. Although low concentration of serum may be tolerated by the cells, it is best to avoid exposing the cells to serum since serum contains many cytokines such as LIF and CNTF which promote glial differentiation of the NSCs. Thus, during passage, the enzyme used is stopped by adding specific enzyme inhibitor, such as trypsin inhibitor, rather than serum. At each passage, the number of harvested cells are counted, and a fraction is re-seeded for further expansion. As illustrated in FIG. 1, using the method of the instant invention, human NSCs can be expanded beyond $10^{18}$-fold increase in population while maintaining their growth and differentiation properties. The cells can be expanded reproducibly. As shown in FIG. 1, serial passaging of the cells have been repeated three times with reproducible growth curve and doubling time of the cells. During the expansion, almost all cells express nestin, the in vivo marker of mitotic neuroepithelial cells, and are absent of antigens of differentiated neurons and glia such as type 3-beta tubulin and GFAP. The cells are also negative by immunostaining for PSA-NCAM, a possible marker of committed neuronal progenitors, O4 and GalC, markers of oligodendrocytes, and RC2, a marker of radial glia. Thus, determined by immunostaining, the NSCs stably maintain their expression of antigen profile throughout the prolonged expansion period. An example of the morphology and the nestin expression is shown in FIGS. 2 A and B, respectively.

Example 2

Differentiation of Human Spinal Cord Neural Stem/Progenitor Cells

At any point during expansion of the NSCs, the cultures can be differentiated by withdrawal of the mitogen in the culture such as bFGF. Differentiation of NSCs ensues within about 1-3 days after the removal of mitogen, and distinct heterogeneous cell morphologies are apparent. By approximately day 4-7 of differentiation, neuron-specific antigens, such as MAP2c, tau, and type III beta-tubulin, can be visualized by immunostaining. By approximately day 12-14, elongated, fasciculated axonal processes are evident throughout the culture along with clear polarization of subcellular protein trafficking. By approximately day 28, synaptic proteins, such as synapsin and synaptophysin, localize into axon terminals, appearing as punctate staining. Additional feeder layer of astrocytes can be provided to further promote long-term maturation of the neurons. As illustrated in FIG. 3, differentiation of human spinal NSCs generates mixed cultures of neurons and glia wherein the neurons robustly express neuron-specific antigens such as tau, MAP2ab (A) and type3 beta tubulin (B) and comprises approximately 50% of the culture. As shown in FIG. 3B, the culture spontaneously generates long, bundled, axon cables that stretch for several centimeters. As illustrated in FIG. 3C, significant proportion of the neurons are GABAergic. Cholinergic motor neurons are also present in the culture (FIG. 3D). Presence of significant GABA neurons in culture predicts usefulness of the human spinal NSCs for treating various neurological conditions caused by decreased GABA production in certain circuitry. Likewise, presence of cholinergic neurons demonstrates that the human spinal NSCs are capable of motor neuron differentiation and predicts their usefulness for treating various motor neuron diseases caused by gradual degeneration of motor neurons. For treatment, the NSCs are expanded with or without further phenotype-enhancing conditions, harvested, and injected into a neural area of deficiency.

Example 3

Expansion of Human Midbrain Neural Stem/Progenitor Cells

Figure 4:
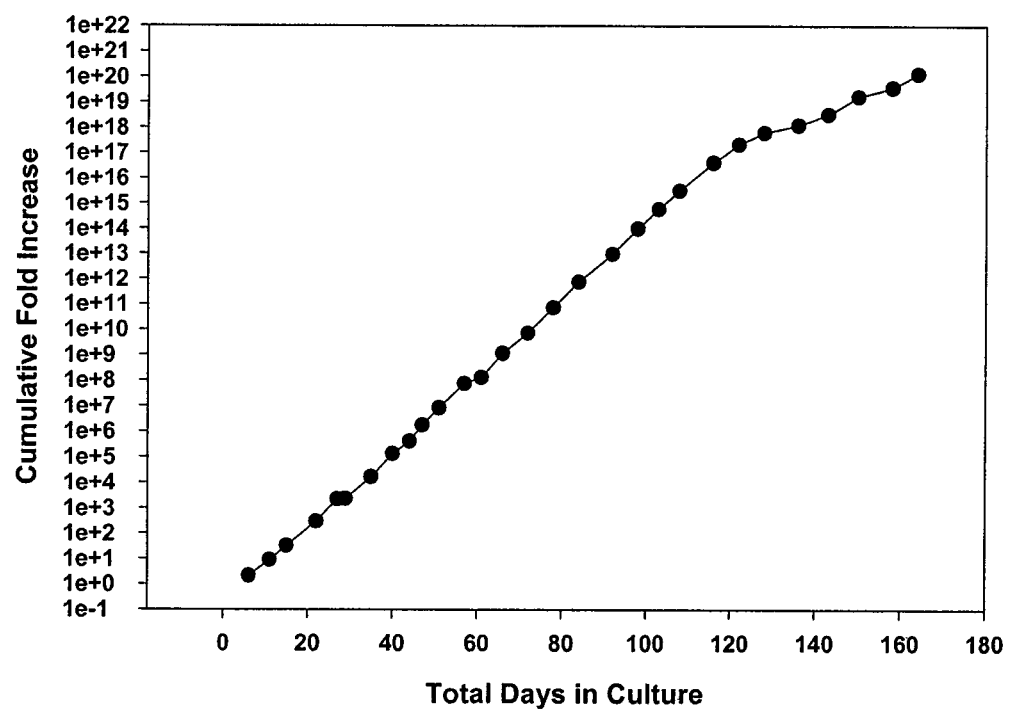
FIG. 4. Expansion of human midbrain stem cells. A human midbrain progenitor (a.k.a. NSC) line was isolated from a 7-8 week old post-mortem fetal mid brain tissue and serially passaged for about 170 days of net culture period. At each passage, the cell number recovered at harvest was divided by the initial cell number at plating to obtain the fold-increase in cell number. Cumulative fold-increase (Y axis) was obtained by multiplying the fold-increase at each passage.

One midbrain tissue of fetal gestational age 7-8.5 week is obtained. NSCs from the midbrain tissue are obtained as described in Example 1. The cells are serially passaged over 160 days of net culture period and the resultant expansion is shown in FIG. 4. Throughout the period of the expansion, the NSCs stably maintain their multipotipotentiality and neurogenic potential as well as their differentiation potential to give rise to dopaminergic neurons. Dopaminergic neurons are assessed by neuronal expression of tyrosine hydroxylase (TH) and dopamine transporter (DAT).

Figure 5:
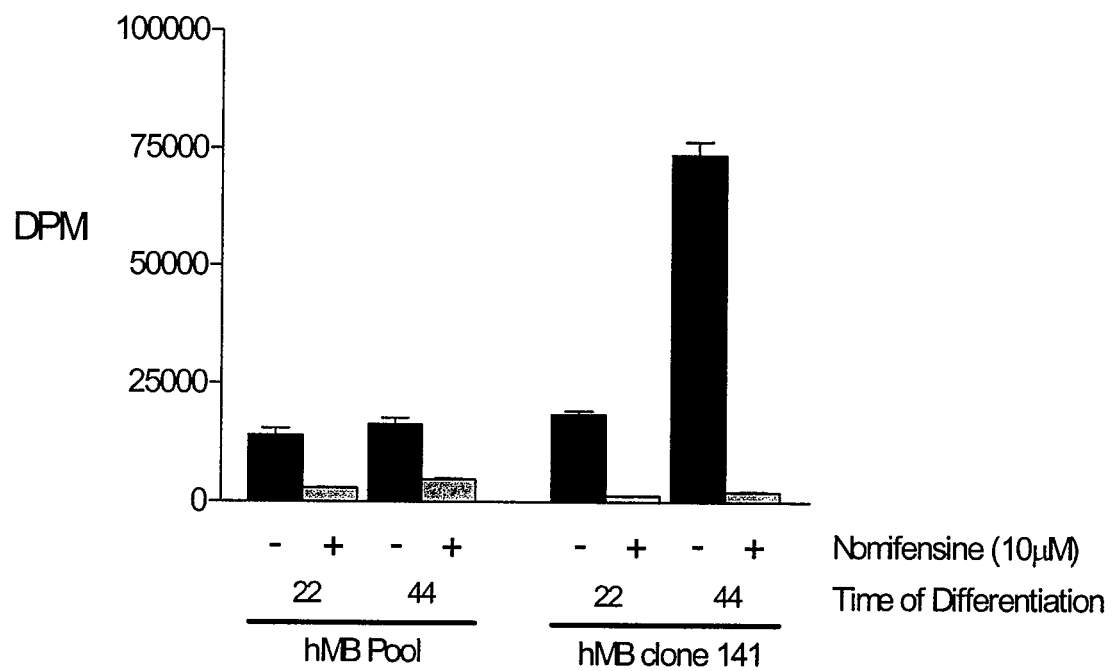
FIG. 5. Dopamine uptake activity of expanded human midbrain stem cells. Dopamine transporter activity (DAT) in live cells was determined from a human midbrain stem cell line and one of its clonal subline, which were differentiated for 22 or 44 days at the time of assay. The cells were incubated with radiolabeled dopamine in the presence (+) or absence (−) of the DAT inhibitor nomifensine (10 μM). Cells were washed to remove unincorporated dopamine and lysed in a scintillation cocktail. The total cellular radioactivity (dpm) was then determined using a scintillation counter.

DAT expression is a marker of dopamine-producing neurons. DAT expression in neurons can be assessed by measuring its function to transport radiolabelled dopamine across the synaptic membrane of differentiated neurons in culture. DAT function in cultures from differentiated human midbrain NSCs and monoclonally derived human midbrain NSCs are assessed by the radiolabelled dopamine uptake assay (FIG. 5). The assay result shows robust functional dopaminergic activity of human midbrain NSCs. Moreover, it illustrates that dopaminergic phenotype can be enriched by isolated monoclonal population of NSC which is particularly inclined to give rise to higher proportion of dopaminergic neurons upon differentiation (FIG. 5).

NSCs generating enriched dopaminergic neurons is particularly useful for treatment of Parkinson's disease. Similarly, NSCs pre-programmed at the time of isolation from the tissue for enhanced differentiation for a specific phenotype can be used to isolate other specific desired neurons, such as forebrain cholinergic neurons useful for treatment of Alzheimer's disease, spinal cholinergic neurons useful for treatment of motor neuron diseases such as ALS, serotonergic neurons useful for treatment of depression, and GABAergic neurons useful for treatment of epilepsy and Huntington's disease.

Example 4

Differentiation of Human Midbrain Neural Stem/Progenitor Cells. Human midbrain NSCs/progenitors can be differentiated as described in Example 2. During the mitotic period of the NSCs or during their differentiation, the proportion of desired phenotype can be enriched by treatment of the culture with various exogenous factors. An example of such factors capable of enriching dopaminergic phenotype from the human midbrain NSCs is demonstrated by the conditioned media from sertoli cells, as illustrated FIGS. 6A and 6B.

Figure 6A:
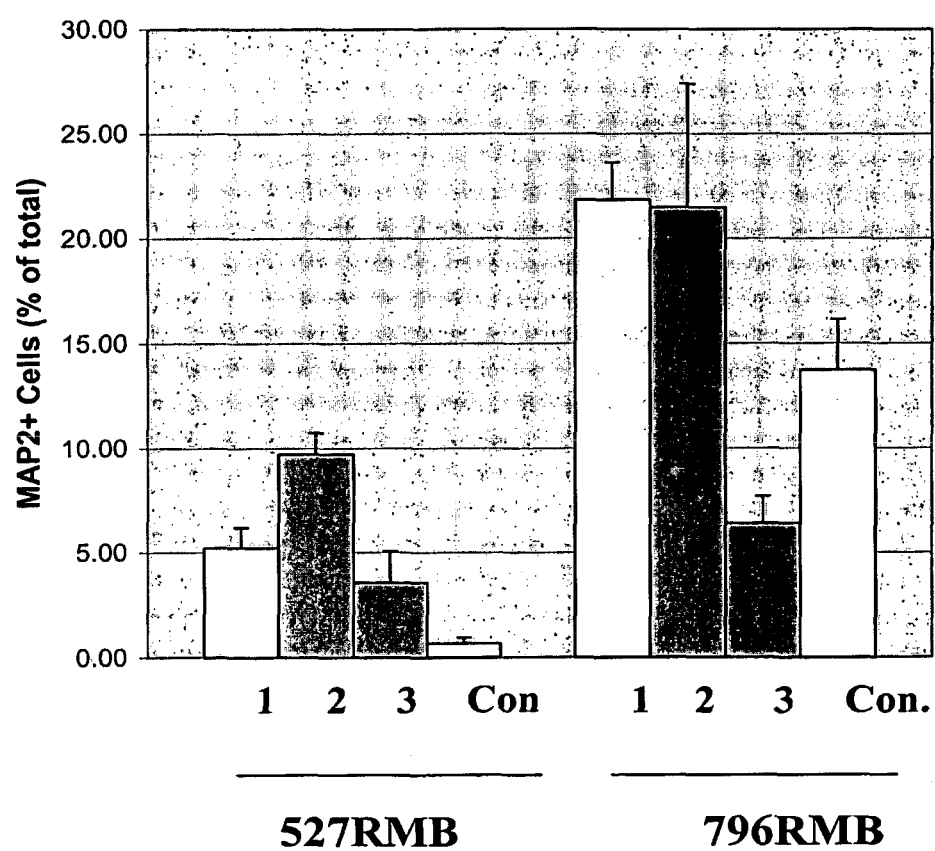
FIG. 6. Effect of exogenous factors on induction of neuronal differentiation and dopaminergic differentiation of human midbrain stem cell lines. Cryopreserved neural stem cells from two human midbrain stem cell lines (527RMB and 796RMB) were thawed and plated at a density of 40,000 cells per well in 4-well chamber slides in the presence of bFGF and allowed to proliferate for 6 days. Subsequently, bFGF was removed and cells were allowed to differentiate for additional 8 days. Cells were divided into four groups based on the timing and duration of exposure to sertoli cell conditioned medium (SCCM, diluted 1:1 in N2). One group was exposed to SCCM during proliferation and differentiation (condition 1); a second was exposed during proliferation only (condition 2); a third was exposed during differentiation only (condition 3); and a fourth was not exposed to SCCM (Control, Cont.). Media was changed every other day, and mitogen was added daily during the proliferative phase. Four wells were maintained per condition to allow staining for multiple markers. Upon differentiation, the cells were fixed using 4% paraformaldehyde and immunostained using antibodies to MAP2ab (FIG. 6A) and tyrosine hydroxylase (FIG. 6B), as well as GFAP and GalC. Immunostained cells were counted using a 40× objective, and at least three fields were counted for each well. Few or no GFAP+ or GalC+ cells were detected upon analysis of cells maintained under any condition, so these antigens were excluded from the analysis.
Figure 6B:
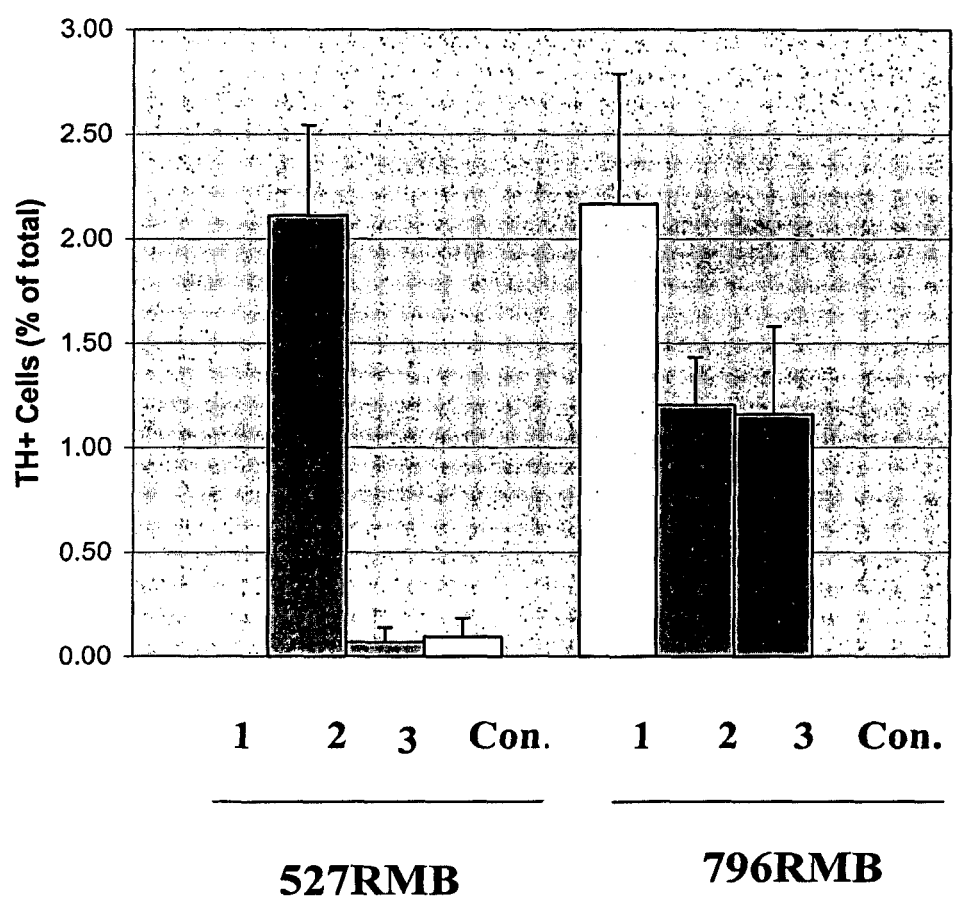

In the studies shown in FIGS. 6A and 6B, cryopreserved neural stem cells were thawed and plated at a density of 40,000 cells per well in 4-well chamber slides in the presence of mitogen and allowed to proliferate for 6 days, at which time mitogen was removed and cells were allowed to differentiate for 8 days. Cells were divided into four groups based on the timing and duration of exposure to sertoli cell conditioned medium (SCCM, diluted 1:1 in N2a). One group was exposed to SCCM during proliferation and differentiation (condition 1); a second was exposed during proliferation only (condition 2); a third was exposed during differentiation only (condition 3); and a fourth was not exposed to SCCM (control or cont.). Media was changed every other day, and mitogen was added daily during the proliferative phase. Four wells were maintained per condition to allow staining for multiple markers, and three cell lines were tested: 796MB, 527MB, and 566SC. 566SC cells, which were derived from spinal cord did not have measurable TH-positive neurons, were omitted from the figure.

Upon differentiation cells were fixed using 4% paraformaldehyde and immunostained using antibodies to MAP2 [AP20 clone (Sigma) which recognizes MAP2ab subtypes], neuron-specific β-tubulin [TuJ1 (Covance)], and tyrosine hydroxylase (Pel-Freez), as well as GFAP (Dako) and GalC (Chemicon). Immunostained cells were counted using a 40× objective, and at least three fields were counted for each well. Few or no GFAP+ or GalC+ cells were detected upon analysis of cells maintained under any condition, so these antigens were excluded from the analysis. In addition, 566SC cells were too dense to quantitate after maintenance under the conditions described and were not included in the final analysis.

The analysis illustrates that the human midbrain NSCs can be influenced by treatment with exogenous factors to search for useful protein factor or chemicals to further enrich for dopaminergic neurons. Thus, novel synthetic/natural chemical and protein factors can be effectively screened by using human NSCs to obtain particularly useful populations for treatment of specific indication such as Parkinson's disease.

Example 5

Treatment of Spasticity and Rigidity in Rats by Transplantation of Human Spinal Neural Stem/Progenitor Cells To induce transient spinal cord ischemia the technique previously described in Taira, (1996) is used. Sprague Dawley (SD) rats are anesthetized in halothane (1.5%). A 2 Fr Fogarty® catheter is passed through the left femoral artery and through the descending thoracic aorta to the level of the left subclavian artery. To measure distal arterial pressure (DBP) below the level of aortic occlusion, the tail artery is cannulated with a polyethylene (PE-50) catheter.

Spinal cord ischemia is induced upon inflation of the intra-aortic balloon catheter with 0.05 mL of saline. Systemic hypotension during the period of aortic occlusion is reproduced by withdrawing a portion of arterial blood (10.5-11 cc) from a carotid artery cannulated with a PE-50 catheter. Systemic hypotension of approximately 40 mm Hg can be induced with this method. The efficacy of the occlusion is evidenced by an immediate and sustained drop in the DBP measured in the tail artery. After approximately 10 minutes of induced spinal cord ischemia, the balloon is deflated, and the blood withdrawn from the carotid artery is reinfused. When the arterial blood pressure is stabilized (within about 20-30 minutes after re-flow), the arterial lines are removed, and wounds are closed.

After the induction of spinal cord ischemia, the recovery of motor function is assessed in approximately 2-day intervals using a modified 21-point open field locomotor scale (BBB scale)). Only animals with a BBB score of 0-4 are selected for the transplantation study for experimental groups).

About 7-21 days following the ischemic lesion, spastic rats with BBB score of 0-4 are anesthetized with 1.5-2% halothane in room air and placed into a spinal unit apparatus. A partial laminectomy of Th11-L2 vertebra is then performed. A glass capillary having a tip diameter of 80-100 µm is connected to a pressure-controlled microinjector. Rats are injected with 0.5 µl of cell suspension containing 5,000, 10,000, 15,000 or 20,000 human neural stem/progenitor cells per injection. Each rat receives a total of 6-8 injections on each side of the spinal cord (left and right), evenly distributed between exposed L2-L6 segments. The center of the injection is targeted into central gray matter (laminae V-VII) (distance from the dorsal surface of the spinal cord at L3 level: 1 mm). After implantation, the incision is cleaned with 3% $H_2O_2$ and a penicillin/streptomycin mixture and closed in 2 layers. Rats are then allowed to recover.

Immunosuppressive treatment with FK-506 (Prograf; Fujisawa; 1 mg/kg; i.p.) is initiated in all animals about 3 days prior to spinal transplantation. Following transplantation, the animals receive immunosuppressive treatment daily during the entire survival period. Immune rejection of these grafts can be effectively prevented with FK-506. The rats survive for approximately 2 or 7 weeks (n=5 for each time point).

At the end of the survival periods, rats are anesthetized with pentobarbital (40 mg/kg; i.p.) and transcardially perfused with heparinized saline for 1-2 min followed by 4% paraformaldehyde in 0.1M phosphate buffer (PB). The spinal cords are dissected and postfixed in the same fixative overnight at 4° C. After post-fixation, spinal cord tissue is cryoprotected in a graded sucrose solution (10, 20 and 30%) for a total of three days. Frozen coronal, parasagittal or horizontal spinal cord sections (10-30 µm) are then cut. For immunohistochemistry, free floating sections (30 µm) are placed in PBS, 0.1M (pH=7.4) containing 5% normal goat serum (NGS), 0.2% Triton X100 (TX), for two hours at room temperature to block the non-specific protein activity. This is followed by overnight incubation at 4° C. with various primary human specific antibodies After incubation with primary antibodies, sections are washed 3× in PBS and incubated with secondary goat anti rabbit or mouse antibodies conjugated to fluorescent marker (Alexa 488 or 594; 4 µl/ml; Molecular Probes). All blocking and antibody preparations are made in 0.1M PBS/0.2% TX/5% NGS. For double labeling experiments, primary antibodies from different species are applied simultaneously, followed by application of secondary antibodies conjugated to different fluorescent markers. In control experiments primary antibodies are omitted. For general nuclear staining, DAPI (3 µl/ml) is added to the final secondary antibody solutions. After staining, sections are dried at room temperature and covered with Prolong anti-fade kit (Molecular Probes).

Slides are analyzed using a Leica Fluorescence microscope. Images (512×512 pixels) are captured with Olympus digital camera and processed by Adobe Photoshop 5.5 (Adobe Systems, Mountain View, Calif.). To confirm co-localization of different antibodies in double stained sections images are captured with a DeltaVision deconvolution microscope system including a Photometrics CCD mounted on a Nikon microscope (Applied Precision, Inc.). In general, sixty optical sections spaced by 0.1 or 0.2 µm are taken. Lenses used are 20×, 40× and 60× (NA 1.3). The data sets are deconvoluted and analyzed using SoftWorx software (Applied Precision, Inc) on a Silicon Graphics Octane workstation.

The total numbers of grafted neurons immunoreactive for the human nuclear NUMA antibody are estimated using stereological, unbiased and systematic sampling. Each tenth, previously-stained section taken from L2-L6 spinal segments is used for stereological quantification after applying fractionator sampling scheme. The optical images (1 µm thick) are obtained by Leica DMLB microscope using a 100× oil immersion objective with numerical aperture 1.3. The optical images are captured using a digital camera (Olympus) and ImagePro software (Media Cybernetics) supplied with a StagePro-controlled motorized Z stage (Media Cybernetics). The total number of grafted cells are then calculated by applying the fractionator formula $N=Q\times 1/\mathrm{hsf}\times 1/\mathrm{asf}\times 1/\mathrm{ssf}$, where N is a total number of positive nuclei, Q is sum of cells counted, hsf is the height sampling fraction, asf is area sampling fraction and ssf is slice sampling fraction.

To provide a three-dimensional reconstructed view of the grafted human NSCs in the ischemic spinal cord, previously stored images taken from serially cut spinal cords are used. On average, about 60-100 serial sections are used for three-dimensional reconstruction. In the first step, a stack of serial images is opened using Ellipse software and aligned using the custom developed Allign module (ViDiTo, SK). The alignment process consists of defining two morphological reference points in all serial spinal cord images (the first point: center of the central canal; the second point: medial border of the dorsal horn), and a subsequent computer-processed alignment of all images. To identify the borders of the dorsal and ventral horns, lines are then draw on the stack of previously aligned images using Laminar Maps module (Ellipse). Finally, the stack of previously aligned and laminar maps-labeled images are used for three-dimensional reconstruction using 3-D constructor (Media Cybernetics).

Culture of human spinal NSCs on rat astrocytes for two to three weeks showed a time dependent maturation and development of neuronal phenotype in the majority of the cultures. This is confirmed by staining with human-specific antibodies against NSE or MOC. Numerous neurons with a well developed axodendritic tree are also identified. The majority (85-90%) of NSE positive neurons are GABA positive, Expression of synaptophysin in axons and dendrites are observed in some MOC positive neurons.

A robust survival of cells when grafted at twenty-one days after ischemic injury is seen. This is expressed as clearly-identified bilateral grafts immunoreactive for NUMA, MOC, or NSE, all human-specific antibodies. Analysis of horizontal sections taken from grafted spinal cord segments show a clear migration of NUMA positive cells between individual injection sites. The majority of NUMA-positive cells show co-localization with MOC immunoreactivity.

Double labeling of spinal cord sections with NUMA and GABA antibodies analyzed with confocal microscopy reveal an average of 25-35% GABA positive cells. A consistent expression of GABA-ergic phenotype is seen in all grafted animals at seven weeks of survival.

At the same time point (i.e. seven weeks after grafting), double-staining with synaptophysin and NUMA antibody show a dense synaptophysin-positive network within the grafts.

Only occasionally will NUMA-positive cells show co-localization with GFAP antibody. These cells are typically localized at the periphery of the grafts.

The stereological estimation of NUMA-positive cells shows an average of 75,460±5,697 persisting grafted cells within individual grafts. This represents an average of 3-3.6 times more cells than originally injected. The cell-cycle antigen, Ki67, is a marker of actively mitotic cells. Staining of spinal cord sections at two or seven weeks after grafting show hKi67 immunoreactivity only at two weeks after grafting. Only occasionally (1-2 cells/10 sections) are cells Ki67-positive at seven weeks of survival. These results indicate that the grafted human spinal NSCs and their progenies expand at a number equivalent to an average of about three cell-doublings for the initial two-week period, which then become postmitotic and stably integrated.

Figure 7:
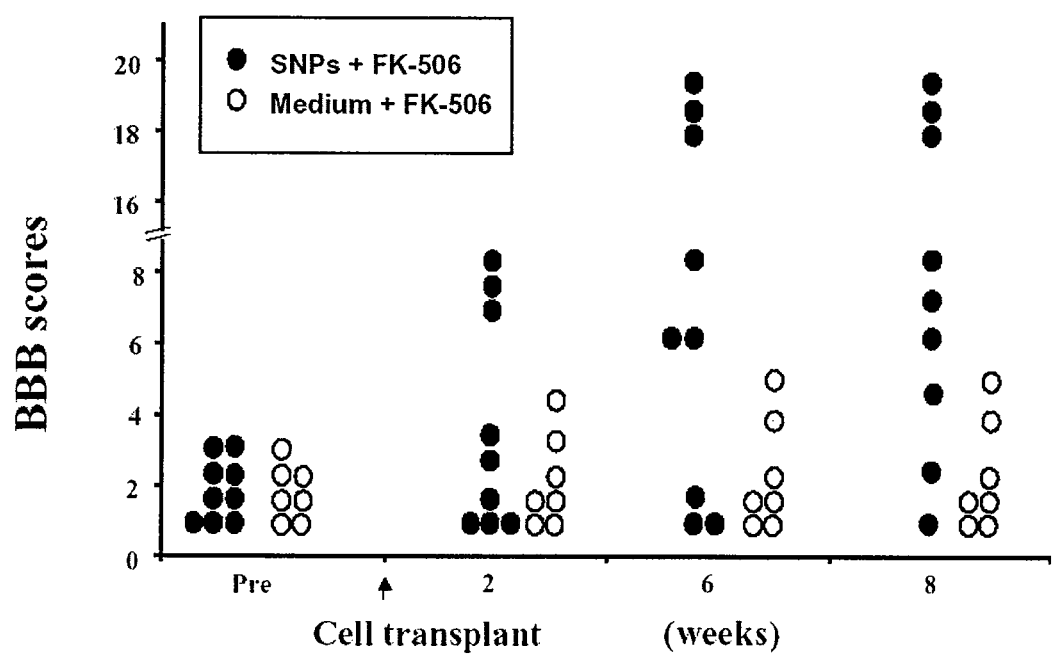
FIG. 7. Reduction of spasticity/rigidity and motor deficits in rats by human spinal stem cell transplantation. Spastic rats were produced by ischemic lesioning of the lumbar spinal cord. In one group (black circle), the rats (n=9) were transplanted with human spinal stem cells expanded in culture (passage 16), while the other, control, group (white circle, n=7) received only the media without the cells. The immunosuppressant, FK506, was administrated at 1 mg/kg daily to both groups for the duration of the study (8 weeks). The motor coordination of individual animals was assessed by BBB scoring once every week.
Figure 8:
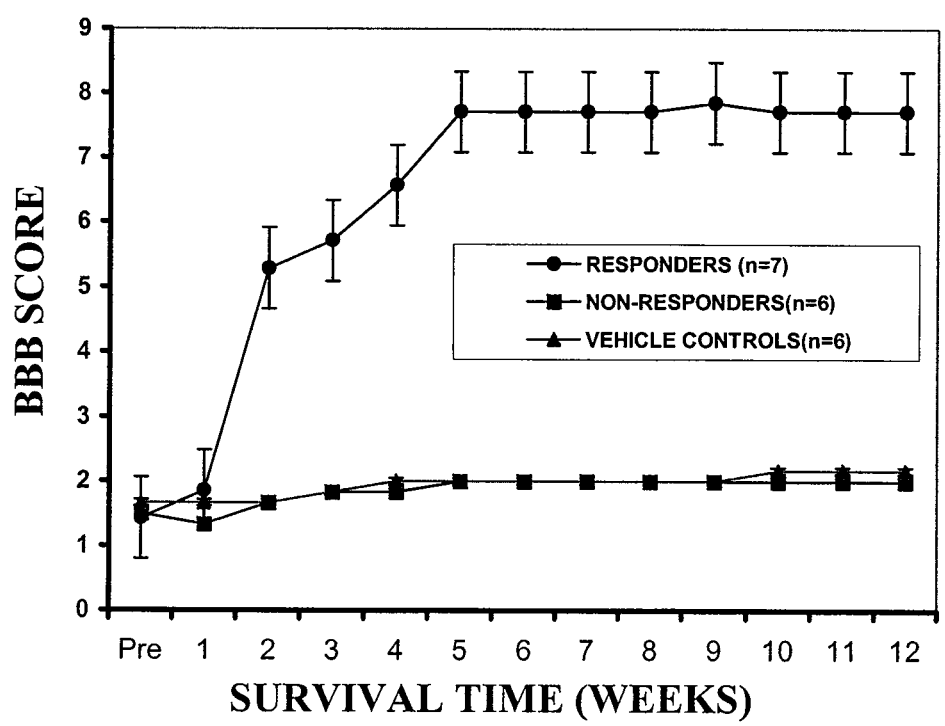
FIG. 8. Reduction of spasticity/rigidity and motor deficits in rats by human spinal stem cell transplantation. Spastic rats were produced by ischemic lesioning of the lumbar spinal cord. In one group (black circle and black squire), the rats (n=13) were transplanted with human spinal stem cells expanded in culture (passage 16), while the other, control, group (filled triangle, n=6) received only the media without the cells. The immunosuppressant, FK506, was administrated at 3 mg/kg daily to both groups for the duration of the study (12 weeks). The motor coordination of individual animals was assessed by BBB scoring once every week.

Volume reconstruction of transplanted L3-L5 segments is performed by using images taken from 40 μm-thick serial spinal cord sections stained with MOC antibody and DAPI (total number of 150-200 sections). Three-dimensional graft reconstruction shows a well recognized rostrocaudally orientated MOC-positive implant distributed within the range of gray matter. As illustrated in FIG. 7 and FIG. 8, the functional effect of the human spinal NSCs are assessed by engrafting the cells and measuring recovery motor benefit by BBB scoring.

With respect to the degree of behavioral recovery observed in the present study we have seen three principal groups after grafting. First, animals which displayed the most robust recovery and the ability to walk (BBB <16), second, animals which showed improvement in the active mobility of all 3 joints in the lower extremities but were not able to stand (BBB around 8), and, the third group in which animals which didn't show any recovery (i.e. non-responders). While the reason for the differences in responsiveness to the grafting is not clear we speculate that a subtle differences in the graft positions with respect to the dysinhibited primary afferents and/or α-motoneurons can play a role. Furthermore it should be noted that animals survived only for 3 months in the present study. We speculate that a long term post-grafting survival and continuing physical rehabilitation will likely be associated with a higher degree of functional recovery. Nonetheless, in contrast to treatment group no significant recovery was seen in any animal injected with medium only.

Example 6

Treatment of Motor Neuron Diseases by Transplantation of Human Spinal NSCs. The NSCs of the disclosed methods afford both clinical and biological benefits that are powerful and significant. To this end, the disclosed methods allow for the treatment of conditions both disseminated throughout the central nervous system, such as ALS, as well as localized in a particular area as in spinal cord ischemia described above. In ALS, although grafting in the lumbar cord may omit other vital portions of the segmental motor apparatus, i.e. the cervical motor neuron column responsible for respiratory movements, the disclosed methods of implanting NSCs in the spinal cord facilitate the release of BDNF and GDNF and other factors from the transplanted cells into the CSF where a broader effect on host motor neurons throughout the cord can occur.

It has been surprisingly found that partial grafts of human NSCs into the lumbar segments of the neurodegenerative spinal cord environment survive, undergo extensive neuronal differentiation and promote motor neuron survival and function both at the site of implantation and at other locations. The NSCs significantly delay the onset of symptoms and extend the life of SOD1 G93A rats, a model of human ALS (amyotropic lateral sclerosis).

The SOD1 G93A rat represents a comprehensive model for the neuropathology and clinical symptoms of an especially aggressive form of ALS. [(Nagai et al., 2001; Howland et al., 2002)] NSCs from human fetal spinal cord can be grafted into the lumbar cord of SOD1 G93A rats and mice where extensive differentiation of the neurons occurs and where the differentiated neurons subsequently form synaptic contacts with host neurons and express and release GDNF and BDNF. The rat SOD1 G93A model, for example, characterized by fulminant motor neuron disease can be used to study and demonstrate the beneficial effects of NSCs in the disease. To this end, NSC grafts employed in the disclosed methods survive well in a neurodegenerative environment and exert powerful clinical effects. At least a portion of these effects is related to the ability of these grafts to express and release motor neuron growth factors. Accordingly, the grafted NSCs of the disclosed methods delay the onset and progression of the fulminant motor neuron disease and extend the life span of these animals by more than ten days, despite the restricted grafting schedule that was limited to the lumbar protuberance.

Human NSCs (NSI-566RSC) from spinal cord tissue of a post-mortem human fetus of eight weeks gestational age are expanded in serum-free medium containing fibroblast growth factor (FGF-2) for about 10-12 passages prior to grafting (Johe et al., 1996). The fate of these cells are reliably traced with antibodies against human nuclear antigens (HNu) (Yan et al., 2003). All surgical procedures using these cells are carried out according to protocols incorporated herein by reference approved by the Animal Care and Use Committee of the Johns Hopkins Medical Institutions using gas anesthesia (enflurane:oxygen:nitrous oxide=1:33:66) and aseptic methods.

Live or dead NSCs are grafted into the lumbar protuberance (L4 & L5) of nine-week old (220-300 g) SOD1 G93A rats of mixed gender mounted on a Kopf spinal stereotaxic unit under microscopic guidance. Dead cells are prepared by repetitive freezing and thawing before grafting. Cell suspensions are delivered under aseptic conditions via approximately eight injections aimed at ventral horn on both sides of the ventral horn ($5 \times 10^4$ NSC per injection site, four injection sites per side) with pulled-beveled glass micro-pipettes connected, via silastic tubing, to 10 μl Hamilton microsyringes. All rats receive FK-506 (1 mg/kg i.p.) to prevent immune rejection based on pilot data indicating that, in untreated animals or animals receiving cyclosporin, graft survival does not exceed one month.

Rats are tested for motor strength and weight twice weekly. Motor strength tests included the Basso, Beattie and Bresnahan (BBB) locomotor rating scale (Basso et al., 1995), and the inclined plane scale (Rivlin and Tator, 1977). For BBB score testing, animals are tested for about 4 or 5 minutes in the open field. All locomotor performance is recorded and rated according to scale. For inclined plane testing, rats are placed on the incline plane mat, and angle is adjusted to the maximal point at which their position can be stabilized for about 5 seconds. This angle is then recorded as the animal's inclined plane score. BBB and incline plane scores are analyzed by MANOVA followed by Fisher LSD post hoc test. Disease onset is defined as the point at which body weight begins to decrease abruptly. Course of illness as an effect of graft type (live- or dead-cell graft) is analyzed by comparing age at disease onset and age of death between the two groups (with students' t test) as well as with Kaplan-Meier survival analysis followed by long-rank test.

Rats are euthanized with perfusion-fixation when their BBB score (see below) is less than 3, a stage at which only one joint has movement or there is no movement at all and the animal is considered moribund.

Tissues are prepared from animals perfused with 4% neutral-buffered paraformaldehyde. The thoraco-lumbar spinal cord segments with attached roots and lumbar nerves are further fixed by immersion in the same fixative for an additional four hours. Blocks containing the entire grafted area plus 1 mm border above and below the block are cryoprotected and frozen for further processing. L3-S1 roots are processed separately as whole-mount preparations or after separating rootlets with heat-coagulated tips of glass pipettes. Blocks are sectioned at the transverse or sagittal plane (35 μm). NSC survival and differentiation is studied with dual-label immunofluorescence that combines, in most cases, HNu, a human-specific marker, with another cellular marker. and is performed as described in Yan et al., 2004.

A non-stereological method of counting total number of HNu (+) cells as well as cells dually labeled with HNu and a phenotypic marker on randomly selected high-power (100×) fields from our immunofluorescent preparations is used to study NSC differentiation. One field in each of six sections spaced ~1 mm apart through the grafting area is used from each animal. Numbers of HNu (+) and double-labeled profiles are pooled from all six fields counted from each case and grouped per experimental protocol. Average numbers of single and double-labeled cells are generated for each treatment group (n=6 per group).

To assess motor neuron survival in rats grafted with live or dead cells (n=4 of each), tissues from animals sacrificed at 128 days of age are evaluated. Every sixth section in the L3-S1 region from each animal is sampled as per stereological requirements (Yan et al., 2004), and α-motor neurons, identified as multi-polar cells with a distinct nucleus and a soma diameter of >35 μm, are counted with the optical fractionator as described in Yan et al., 2004. Differences between animals grafted with live versus dead cells are analyzed with students' t test.

For ELISA determination of motor neurotrophic factors, CSF is sampled with a 25 G syringe from the 4th ventricle of animals under gas anesthesia. Tissue samples containing the grafting sites and areas adjacent to those are dissected transversely from 1-mm-thick fresh spinal cord slices. CSF or tissue samples are processed, and total protein is first measured as described in Sheng et al., 2003. Levels of GDNF and BDNF are measured in CSF and spinal cord samples using the E-Max ImmunoAssay system (Promega, Madison, Wis.). TMB-chromogen absorbance is read at 450 nm. Variance in concentrations among samples from live grafts, areas adjacent to grafts and dead-cell grafts is analyzed with one-way ANOVA followed by Tukey's Multiple Comparison post hoc test. Difference in CFS concentration between animals grafted with live versus dead cells is analyzed with students' t test.

For western blotting of motor neurotrophic factors, Protein samples from CSF or spinal cord prepared as for ELISA are electrophoresed with molecular weight markers and transferred to nitrocellulose membranes. Blots are blocked in TBS, pH 7.4, containing 5% donkey serum and then incubated in GDNF and BDNF antibodies (1:500; overnight, 4° C.) first, and then in HRP-linked donkey anti-goat IgG (for GDNF) and anti-rabbit IgG (for BDNF) (1:2000; Jackson ImmunoResearch)(1 hr, RT). All antibodies are diluted in TBS containing 5% donkey serum. Blots are developed with the SuperSignal Chemiluminescent Substrate (Pierce) and exposed to Kodak-XAR film (Eastman Kodak, Rochester, N.Y.). Blots are then striped and re-blotted with β-actin antibody (1:500, Sigma) and HRP-linked donkey anti-mouse IgG (1:10000, Jackson ImmunoResearch). Immunoreactive bands are analyzed with Bio-Rad Quantity One software (Bio-Rad Laboratories, Hercules, Calif.). Band density ratios (GDNF or BDNF: β actin) are calculated per animal and group means are entered for statistical analysis as in the case of ELISA experiments.

Human NSCs in the spinal cord of SOD1 G93A rats at 22 weeks post-grafting are identified by immunostaining with human-specific HNu antibody. HNu (+) cells are shown to survive in the ventral horn (A) and to stain, in their vast majority, with neuronal lineage markers such as the microtubule-associated epitope TUJ-1. Human NSCs are identified by their human nuclear protein (HNu) signature and their phenotypic fates are tracked with dual immunocytochemistry for HNu and epitopes specific for neural precursor, neuronal and glial cells. At the end of experiments in SOD1 G93A rats, human NSCs show robust engraftment and excellent long-term survival. A majority of HNu(+) cells (70.4±6.4%) differentiated into the neuronal lineage based on their co-localization of TUJ-1. Approximately one-fifth (19.2±5.6%) of HNu(+) cells colocalized with nestin and very few (1.3±0.9%) HNu(+) cells were positive for GFAP.

The capacity of human NSCs to integrate within the host circuitry is tested with perikaryal markers for graft/host cells and markers selective for either host or graft terminals. Sections are stained for HNu to establish graft origin, TUJ-1 to establish neuronal differentiation, and a monoclonal antibody for the pre-synaptic protein Bassoon (BSN) that recognizes rat and mouse epitopes, but not human epitopes. A large number of HNu(+), TUJ-1(+) cells in parenchymal locations are found to be contacted by synaptic boutons of rat origin.

In confocal microscopy, NSC-derived neuronal cells with HNu (+) nucleus and TUJ-1 (+) cytoplasm are contacted by rat terminals Conversely, preparations stained with TUJ-1 and human-specific synaptophysin reveal dense terminal fields of small boutons apposed to host neurons, especially large and small motor neurons. A host motor neuron is contacted by a large number of graft-derived boutons. Horizontal sections stained for HNu and human NF-70 show a large number of graft-derived axons leaving the graft on the left and coursing preferentially along the white matter of the ventral funiculus. Cells/processes with ChAT immunoreactivity, are used to delineate gray from white matter in the ventral horn. A large number of axons labeled with human-specific antibodies against the neurofilament epitope NF70 are found in association with the grafting sites, evidence that many human NSCs differentiate into projection neurons; these axons show a preference for the white matter of the ventral horn.

Figure 9:
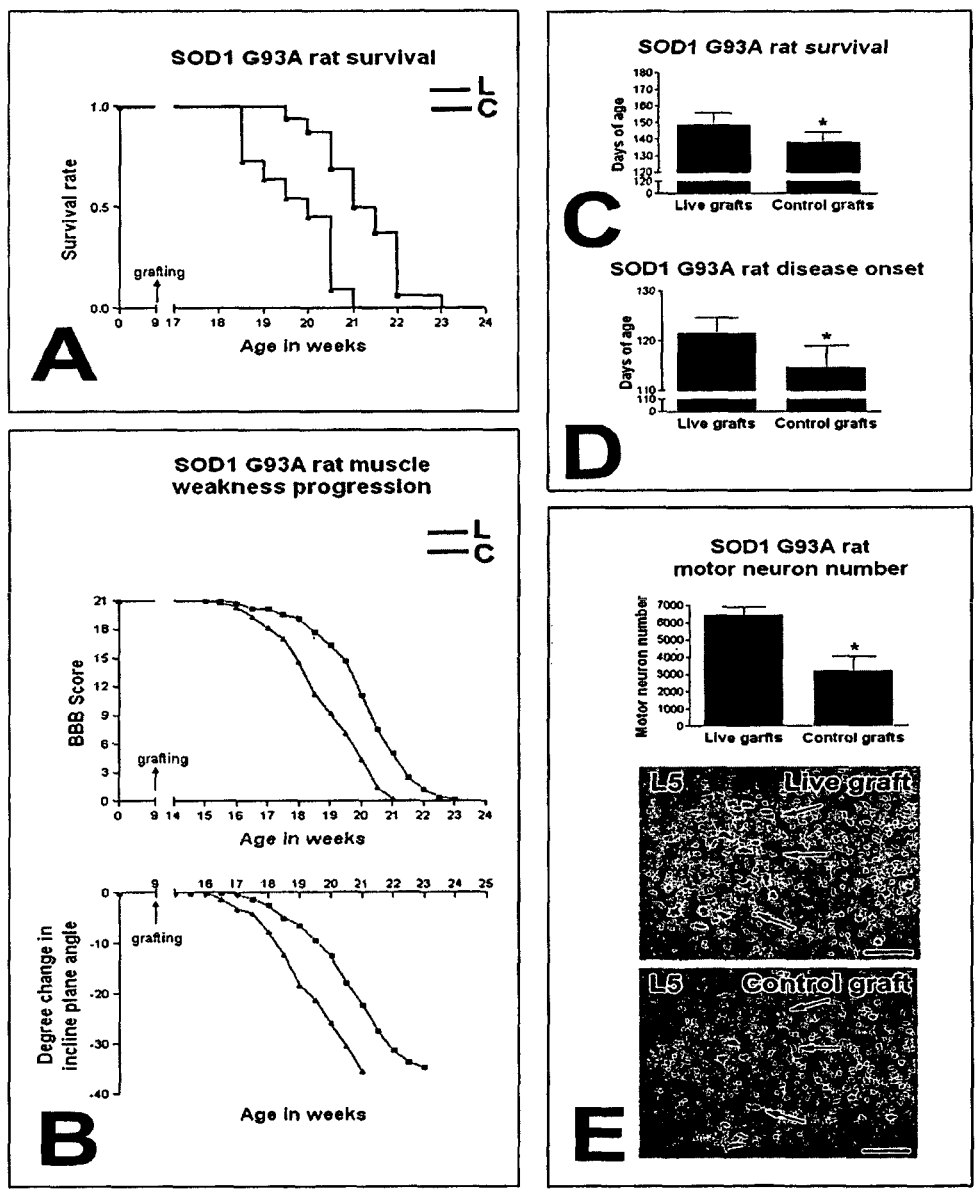
FIG. 9. Effects of human NSC treatment on severity of motor neuron disease in G93A SOD1 rats shown with progression (A-B) as well as end-point (C-E) analysis of clinical and pathological measures in cases with live-cell (L, red) and dead-cell (control, C) grafts (blue).

NSC grafts into the lumbar cord of SOD1 G93A rats prolong life span and delay motor neuron death and disease onset and progression. A progression analysis of clinical and pathological measures in cases with live-cell (L) and dead-cell (control, C) grafts is illustrated in FIG. 9. Animals grafted with live NSCs showed a significantly increased survival by both Kaplan-Meier and end-point analysis. A Kaplan-Meier plot (FIG. 9A) shows a significant separation between experimental and control animals throughout the course of observation (P=0.0003). Time plots of BBB open field and inclined plane test scores (FIG. 9B) show a significantly slower progression in muscle weakness in animals grafted with live NSCs compared to animals that had received dead NSCs.

The effect of NSCs on motor neuron survival in the lumbar protuberance (L3-S1) of Tg rats is examined in a small group of animals that receive live or dead NSCs and euthanized at 128 days of age. The average life span for animals grafted with dead NSCs is 138 days, whereas rats grafted with live NSCs live for 149 days. Therefore, a significant 11-day difference in life span occurs between experimental and control rats (P=0.0005). An average time-to-disease-onset is 115 days for animals that receive dead cells and 122 days for animals that are grafted with live NSCs. A significant 7-day difference is observed in time-to-disease-onset between the two groups (P=0.0001).

Stereologically estimated numbers of α-motor neurons are 6,418 for animals that receive live NSCs and 3,206 for rats that are grafted with dead NSCs, i.e. there are twice as many neurons in the lumbar protuberance of experimental compared to control animals of the same age. A difference of 3,212 cells in the lumbar protuberance between live and dead NSC groups is observed (P=0.01) in a representative experimental and control rat at 128 days of age.

Potential mechanisms of neuroprotection afforded by human NSCs on degenerating motor neurons include the expression and release of, two peptides with classical trophic effects on mammalian motor neurons, [BDNF and GDNF] (Henderson et al., 1994; Koliatsos et al., 1993). Expression and release of GDNF and BDNF in the spinal cord of grafted SOD1 G93A rats is determined. Cord preparations and CSF samples are evaluated for BDNF and GDNF by Western blotting and ELISA. GDNF concentrations in the parenchyma and CSF of rats grafted with live cells (L1 and L2) and animals grafted with dead cells (C) are determined by ELISA. L1 represents concentrations through the grafting site, whereas L2 reflects concentrations in tissues one segment above or below. Variance among groups is significant and caused by a large difference between L1 or L2 and C groups.

Difference in CSF concentrations between experimental (live-cell, L) and control (dead-cell, C) groups is also significant by t test. ELISA showed a concentration of 0.912±0.050 pg/µg at the graft site and 0.819±0.115 pg/µg one segment away in the spinal cord of live NSC-grafted animals. In animals grafted with dead NSCs, these concentrations were 0.368±0.026 pg/µg in spinal cord segments containing the graft. In the CSF, GDNF concentration was 0.027±0.012 pg/µl in experimental and 0.006±0.002 pg/µl. These data demonstrate a three-fold increase in the expression and release of GDNF in the cord and a five-fold increase in GDNF secretion in the CSF of animals with live NSCs.

Western blotting also shows a higher normalized GDNF concentration in animals grafted with live NSCs. GDNF Western blotting confirms the ELISA pattern of increase by detecting a 16 kDa protein. Western blotting also shows a normalized GDNF density of 0.860±0.007 in live-cell grafts and 0.708±0.052 in dead-cell grafts.

ELISA staining of BDNF in the parenchyma and CSF of experimental rats and controls are determined. ELISA analysis shows a concentration of 0.086±0.014 pg/µg at the graft site (L1) and 0.054±0.009 pg/µg one segment away from graft in experimental animals (L2). In control rats, the BDNF concentration was 0.010±0.003 pg/µg in graft-containing segments. The differences between experimental and control CSF concentrations are significant. In the CSF, BDNF concentration is 0.041±0.013 pg/µl in experimental animals and 0.010±0.008 pg/µl in controls. These findings indicate an eight-fold increase in BDNF concentration in the spinal cord and four-fold increase in the CSF of experimental animals. Together, the ELISA data suggest a more widespread secretion of GDNF compared to BDNF in animals grafted with live NSCs, especially in the CSF.

Immunocytochemistry also reveals that the vast majority of grafted HNu(+) cells are expressing GDNF. The source of the GDNF in animals with live grafts is the grafted cells themselves. In the dually stained preparations for HNu (red) and GDNF (green) illustrate the abundance of GDNF immunoreactivity within the cytoplasm of grafted NSCs. In animals that receive live grafts, there is intense GDNF immunoreactivity in round cytoplasmic structures resembling secretory vesicles within host motor neurons.

Confocal microscopy through a host motor neuron stained with GDNF and human synaptophysin (the latter to label graft-derived terminals) indicates the localization of GDNF in vesicular structures but not in graft-derived terminals located on the surface of the illustrated host motor neuron. Sections stained with human synaptophysin antibodies (to label all graft terminals innervating host motor neurons) and GDNF show lack of any co-localization of the two proteins in boutons contacting host motor neurons.

Rats with live grafts show an elaboration of pathways originating in the graft and innervating structures in and around the central canal. In contrast to the absence of GDNF protein in terminals contacting host motor neurons, the vast majority of NSC-derived axon terminals innervating the central canal co-localizes with GDNF immunoreactivity. Widespread co-localization of human synaptophysin and GDNF is observed within graft-derived terminals innervating ependymal cells in the central canal. These anatomical patterns indicate that GDNF is probably taken up by host motor neuron terminals that innervate the graft via retrograde transport and not delivered to these neurons via trans-synaptic transfer (Rind et al., 2005)

The apparent resistance of grafted NCSs to the ongoing degenerative process in the ventral horn of SOD1 G93A rats is especially promising. The survival and extensive differentiation of NSCs reported here is a strong indication that the inflammatory/excitotoxic signaling involving motor neurons harboring SOD1 G93A (Rothstein et al., 1992; Howland et al., 2002; Turner et al., 2005) has no evident toxicity on cells. This factor alone raises optimism for future cellular strategies using grafts to restore motor function in degenerative motor neuron disease.

Example 7

Treatment of traumatic spinal cord injury by transplantation of human spinal cord neural stem/progenitor cells. treatment of syringomyelia.

Expanded human spinal stem cells were injected into either immunosuppressed, adult female Sprague-Dawley or immunodeficient, a thymic nude rats. $C_{4-5}$ contusion lesions were produced in both groups one month prior to transplantation. The graft recipients (n=24) survived from 60-150 d post-transplantation. The human-derived NSCs formed large cellular aggregates consisting of neurons, astrocytes and oligodendrocytes. These grafts invariably and completely filled each lesion. Immature-appearing, NeuN+/human nuclei+ neurons often comprised 50% of the donor cell population. These neurons sent human neurofilament+ processes through both gray and white matter for distances of at least 2 cm from the graft site. Intense human-specific synaptophysin immunoreactivity was noted in proximity of both host and graft neurons, and seemingly unreactive, GFAP+ cells were juxtaposed with the donor neurons. Further, these transplants supported the growth of TH+ and 5HT+ fibers that appeared to arise from host sources. This line of NSC's thus appears to possess primary fetal CNS-like qualities favorable to intraspinal gray matter repair.

It should be understood that various changes and modifications to the presently preferred embodiments described herein will be apparent to those skilled in the art. Such changes and modifications can be made without departing from the spirit and scope of the disclosed methods and without diminishing its intended advantages. It is therefore intended that such changes and modifications be covered by the appended claims.

The invention is claimed as follows:

1. A method of treating a subject with amyotrophic lateral sclerosis (ALS) comprising:
   a) isolating neural stem cells of human origin from a central nervous system tissue that comprises fetal spinal cord tissue;
   b) expanding in vitro the isolated neural stem cells in a dispersed adherent culture to form an expanded population of neural stem cells, wherein expanding the isolated neural stem cells comprises:
      i.) providing at least one extracellular protein to a culture vessel, wherein the extracellular protein includes at least about 10 µg/mL of poly-D-lysine and less than about 1 mg/ml fibronectin;
      ii.) culturing the dissociated neural stem cells in said culture vessel in the absence of serum;
      iii.) adding to the culture vessel at least one growth factor; and
      iv.) passaging the cultured cells prior to confluence;
   c) concentrating the expanded population of neural stem cells to a density of about 1,000 to about 200,000 cells/µL to form concentrated neural stem cells; and
   d) injecting a therapeutically effective amount of said concentrated neural stem cells into one or more areas of a spinal cord of the subject.

2. The method of claim 1, wherein the neural stem cells are multipotential.

3. The method of claim 1, wherein the neural stem cells are derived from human embryonic stem cells.

4. The method of claim 1, wherein the fetal spinal cord tissue is obtained from a post-mortem fetus having a gestational age of about 6.5 to about 20 weeks.

5. The method of claim 1, wherein the growth factor is selected from the group consisting of bFGF, EGF, TGF-alpha, aFGF and combinations thereof.

6. The method of claim 1, wherein the neural stem cells are expanded to confluence.

7. The method of claim 1, wherein the injected neural stem cells generate at least 1,000 GABA-producing neurons in said tissue.

8. The method of claim 1, wherein said concentrating step c) comprises concentrating the expanded population to a density of about 5,000 cells/µL to about 50,000 cells/µl.

9. The method of claim 1, wherein said injecting step d) comprises multiple injections of the concentrated neural stem cells.

10. The method of claim 1, wherein at least 1,000 cells from said concentrated neural stem cells are injected to the spinal cord of the subject.

11. The method of claim 1, wherein at least 20% of the concentrated neural stem cells differentiate into neurons in the spinal cord of an animal.

12. The method of claim 1, wherein said concentrated neural stem cells are injected into the ventral horn area of the spinal cord.

13. The method of claim 1, wherein said concentrated neural stem cells are injected into the lumbar spinal cord.

14. The method of claim 1, wherein 0.1 to 100 µL of said concentrated neural stem cells are injected into one or more areas of a spinal cord of the subject.

* * * * *